US006107021A

United States Patent [19]
Wang et al.

[11] Patent Number: 6,107,021
[45] Date of Patent: Aug. 22, 2000

[54] SYNTHETIC PEPTIDE VACCINES FOR FOOT-AND-MOUTH DISEASE

[75] Inventors: Chang Yi Wang, Cold Spring Harbor; Ming Shen, Flushing, both of N.Y.

[73] Assignee: United Biomedical, Inc., Hauppauge, N.Y.

[21] Appl. No.: 09/100,600

[22] Filed: Jun. 20, 1998

[51] Int. Cl.$^7$ .............................. C12Q 1/70; A61K 38/00
[52] U.S. Cl. .............................. 435/5; 530/324; 530/300; 536/23-72; 930/22
[58] Field of Search ................................ 435/5; 530/324, 530/300; 536/23.72; 930/220

[56] References Cited

U.S. PATENT DOCUMENTS

| | | |
|---|---|---|
| 4,732,971 | 3/1988 | DiMarchi et al. . |
| 5,106,726 | 4/1992 | Wang . |
| 5,476,765 | 12/1995 | Wang . |

FOREIGN PATENT DOCUMENTS

| | | |
|---|---|---|
| WO 83/03547 | 10/1983 | WIPO . |
| WO 91/03255 | 3/1991 | WIPO . |
| WO 94/25060 | 11/1994 | WIPO . |
| WO 95/11998 | 5/1995 | WIPO . |

OTHER PUBLICATIONS

Fred Brown, *Vaccine*, 10:1022–1026 (1992).
F. Brown, *J. Gen. Microbiol.* (31) pp. 179–186 (1963).
D.O. Morgan, et al., *Am. J. Vet. Res.*51:40–45 (1990).
M.J. Francis, et al., *Immunol.*, 69:171–176 (1990).
E. Pfaff, et al., *The EMBO Journal*, 1:869–874 (1982).
R. Acharya, et al., *Nature*, 337:709–716 (1989).
M.L. Valero, et al., *Biomedical Peptides, Proteins & Nucleic Acids*, 1:133–140 (1995).
C.D. Partidos, et al., *J. of Gen. Virology*, 72:1293–1299 (1991).
H. Gras–Masse, et al., *Peptide Research*, 5:211–216 (1992).
T. Collen, et al., *J. of Gen. Virology*, 71:309–315 (1990).
T. Collen, et al., *J. of Immunol.*, 146:749–755 (1991).
A. Rodriguez, et al., *Virology*, 205:24–33 (1994).
O. Taboga, et al., *J. of Virology*, 71:2606–2614 (1997).
P. Zamorano, et al., *Virology*, 212:614–621 (1995).
M.–J.C. Van Lierop, et al., *Immunology*, 84:79–85 (1995).
K. Strohmaier, et al., *J. Gen. Virol.*, 59:295–306 (1982).
S.J. Barteling, et al., *Vaccine*, 9:75–88 (1991).
J. Lubroth, et al., *Vaccine*, 14:419–427 (1996).
M.J. Laporte, et al., *C.R. Acad. Sc. Paris*, 276, Série D, pp 3399–3401 (1973).
R.H. Meloen, et al., *Ann. Biol. Clin.*, 49:231–242 (1991).
B.P. Babbitt, et al., *Nature*, 317–359–361 (1985).
G.E. Meister, et al., *Vaccine*, 13:581–591 (1995).
K.B. Cease, et al., *Proc. Natl. Acad. Sci USA*, 84:4249–4253 (1987).
S.J. Brett, et al., *Eur. J. Immunol.*, 23:1608–1614 (1993).
C. Ferrari, et al., *J. Clin. Invest.*, 88:214–222 (1991).
A.J. Stagg, et al., *Immunol.*, 79:1–9 (1993).
C.Y. Wang, et al., *Science*, 254:285–288 (1991).
*Science*, 214:1125–1129 (1981).
Synthetic Peptides, A User's Guide, edited by Gregory A. Grant, pp. 63–67 and p. 281 (1992).

*Primary Examiner*—Ali Salimi
*Attorney, Agent, or Firm*—Morgan & Finnegan, LLP

[57] ABSTRACT

The present invention relates to the use of a peptide composition as an immunogen, with each peptide contained therein comprising a target antigenic site derived from the VP1 capsid protein of Foot-and-Mouth Disease Virus (FMDV). The antigenic site is covalently linked to a helper T cell epitope and, preferably, to other immunostimulatory sequences, preferably by conventional peptide bond(s) through direct synthesis, for the prevention of FMDV infection and eradication of Foot-and-Mouth Disease (FMD). More particularly, the present invention relates to the use of such peptide composition as an immunogen to elicit the production in animals including swine, cattle, sheep, goats and susceptible wild species, of high titer polyclonal antibodies that can effectively neutralize, in vitro, multiple strains or serotypes of FMDV, and to the use of such composition as a vaccine to prevent, and/or reduce the incidence of, FMDV infection regardless of serotype, and thus affect the eradication of FMDV. The present invention also relates to the peptides used in the compositions, and to immunoassays and/or diagnostic kits containing one or more of these peptides, and methods of diagnosing FMDV in mammals using such materials.

10 Claims, 4 Drawing Sheets

A SSAL(1) (COMPLETE)(134-169) (SEQ ID NO:14):

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| $N_{10}$ | K | Y | $S_6$ | $V_{14}$ | $S_{11}$ | G | $S_{17}$ | $G_{13}$ | $R_{17}$ | R | G | D | $L_{11}$ | $G_{18}$ | $S_{12}$ | L | A | $A_{17}$ | R | V | $A_{17}$ | $K_{14}$ | $Q_{13}$ | L | P | $A_{19}$ | S | F | N | $Y_{17}$ | G | A | $I_{19}$ | $K_{17}$ |
| $S_9$ | | | $T_{10}$ | $A_6$ | $G_8$ | | $T_1$ | $N_7$ | $V_3$ | | | | $M_6$ | $E_2$ | $P_8$ | | | $P_3$ | | | $V_3$ | $R_3$ | $A_7$ | | | $T_1$ | | | | $F_3$ | | | $V_1$ | $Q_3$ |
| $G_1$ | | | $A_4$ | | $D_1$ | | $M_2$ | | | | | | $F_3$ | | | | | | | | | $A_3$ | | | | | | | | | | | | |

Fig. 2A

A SSAL(1) (COMPLETE)[134(N→C)-158(Q→C)-169] (SEQ ID NO:15)

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| C | K | Y | $S_6$ | $V_{14}$ | $S_{11}$ | G | $S_{17}$ | $G_{13}$ | $R_{17}$ | R | G | D | $L_{11}$ | $G_{18}$ | $S_{12}$ | L | A | $A_{17}$ | R | V | $A_{17}$ | $K_{14}$ | C | L | P | $A_{19}$ | S | F | N | $Y_{17}$ | G | A | $I_{19}$ | $K_{17}$ |
| | | | $T_{10}$ | $A_6$ | $G_8$ | | $T_1$ | $N_7$ | $V_3$ | | | | $M_6$ | $E_2$ | $P_8$ | | | $P_3$ | | | $V_3$ | $R_3$ | | | | $T_1$ | | | | $F_3$ | | | $V_1$ | $Q_3$ |
| | | | $A_4$ | | $D_1$ | | $M_2$ | | | | | | $F_3$ | | | | | | | | | $A_3$ | | | | | | | | | | | | |

Fig. 2B

A SSAL(2) (COMPLETE)(134-169)  (SEQ ID NO:16)

Fig. 3A

A SSAL(2) (COMPLETE)[134(N→C)-158(Q→C)-169]  (SEQ ID NO:17)

Fig. 3B

O SSAL (COMPLETE)(134-169) (SEQ ID NO:18)

O SSAL (COMPLETE)[134-158(T→C)-169] (SEQ ID NO:19)

SYNTHETIC PEPTIDE VACCINES FOR FOOT-AND-MOUTH DISEASE

FIELD OF THE INVENTION

The present invention relates to the use of a peptide composition as an immunogen, with each peptide contained therein comprising a target antigenic site derived from the VP1 capsid protein of Foot-and-Mouth Disease Virus (FMDV), with said antigenic site covalently linked to a helper T cell epitope and, preferably, other immunostimulatory sequences, preferably by conventional peptide bond (s) through direct synthesis, for the prevention of FMDV infection and eradication of Foot-and-Mouth Disease (FMD).

More particularly, the present invention relates to the use of such peptide composition as an immunogen to elicit the production in animals including swine, cattle, sheep, goats and susceptible wild species, of high titer polyclonal antibodies that can effectively neutralize, in vitro, multiple strains or serotypes of FMDV, and to the use of such composition as a vaccine to prevent and/or reduce the incidence of FMDV infection regardless of serotype.

The present invention also relates to the peptides used in the compositions, and to immunoassays and/or diagnostic kits containing one or more of these peptides, or segments thereof.

BACKGROUND OF THE INVENTION

Foot-and-mouth disease (FMD) is the most economically significant disease of domestic livestock. Cloven-hoofed animals of the order Artiodactyla, such as cattle, pigs, sheep and goats, are susceptible. The causative agent, foot-and-mouth disease virus (FMDV), is an aphthovirus of the Picornaviridae family having a positive sense RNA genome encoding four capsid proteins (VP1–VP4) and non-structural polypeptides. The FMDV genome, the coding region for capsid and non-structural proteins and the processing pathway by which proteins are cleaved is shown schematically in FIG. 1 (taken from Tesar et al., Virus Genes, 1989; 3:29–44).

FMD is controlled by quarantine and destruction of infected and exposed animals, and by vaccination with chemically inactivated virus compositions. A significant difficulty for formulation of these vaccines is the remarkable antigenic diversity of FMDV. Seven distinct serotypes have been described: A, O, C, Asia, and the South African types SAT-1, 2, and 3, each of which can be subdivided into multiple subtypes. Viruses of serotypes A, O, and Asia are most common. Serotype A viruses are the most variable, having more than 30 subtypes.

There is no cross-protection between serotypes, therefore animals recovered from infection with or vaccinated against a virus of one serotype are still susceptible to infection with viruses from the remaining six serotypes. Moreover, the degree of antigenic variation within a serotype is such that a vaccine effective against one subtype may not be protective against another subtype within that same serotype. Accordingly, current vaccines are based on a mixture of inactivated viruses comprising a reference strain of each relevant serotype or subtype, as determined by monitoring the virus strains in local circulation. Periodic surveillance on the antigenic relationship between field isolates, including emerging variants, and the viruses being used for vaccine preparation are required to prevent outbreaks.

Therefore, the production of current vaccines requires that several virus strains must be grown and inactivated, with the potency of each assured, and the product must be reformulated periodically with current field strains to prevent loss of protective efficacy by emergence of new variants. The process of preparing multiple virus strains for maintenance of immunogenic efficacy in the face of antigenic variation results in burdensome problems with strain to strain variability in potency and yield during manufacture.

The need for an inactivated virus vaccine for periodic revision in turn generates a new obstacle to vaccine manufacture. When a vaccine is revised to meet the challenge of an outbreak by a newly evolved field strain, the outbreak strain must be artificially adapted to efficient growth in tissue culture. Furthermore, the selection process for adaptation if newly emerging subtypes to tissue culture can result in diminished protective immunogenicity, resulting in further delays in production. (Barteling and Vreeswijk, Vaccine, 1991; 9: 75–88 Brown, Vaccine, 1992; 10: 1022–1026).

Other significant shortcomings of inactivated FMDV vaccines are associated with issues of biosecurity and stability. The virus must be produced in a high-containment facility to prevent contamination of the immediate environment. This potential hazard limits qualified vaccine suppliers to a few, limits the available supply of vaccine, and hampers efforts to respond to outbreaks in previously FMDV-free regions of the world. The innocuousness of the inactivated virus product cannot be ensured absolutely. Several recent cases of the disease in Europe have been traced to incompletely inactivated virus. This hazard discourages use of the vaccines in areas where disease is absent, leaving previously unaffected areas devoid of immune protection.

Product instability as well as to lot-to-lot variability stems from the complex and undefined composition of the inactivated virus vaccines. These complex mixtures must be inspected at regular intervals to ensure immunopotency. In some countries this can be as frequent as three times each year. A cold cabin is necessary to maintain the potency of the unstable product, and frequently this is difficult to ensure in some countries.

A potential for deleterious effects is an additional consequence of the complex composition. Anaphylactic shock is an infrequent problem but nevertheless it occurs sufficiently often to pose problems. These disadvantages are reviewed in Brown, Chapter 11 in *Molecular Aspects of Picornavirus Infection and Detection*, eds Semler and Ehrenfeld, American Society for Microbiology: Washington, DC, 1989, pp 179–191. A further disadvantage stemming from the complex composition of current FMDV vaccines is that it is difficult to distinguish by serological testing animals that have been vaccinated from animals which have been infected (Lubroth et al., Vaccine, 1996; 14: 419–427). A vaccine based on site-specific immunogens would facilitate the design of immunodiagnostic kits to distinguish vaccine-induced antibodies from antibodies induced by infection, and thus ensure the effectiveness of vaccination programs.

The disadvantages of the existing commercial vaccines have encouraged research to replace them with safer and better defined subunit products. However, to be acceptable, such products will need to be of immunogenicity equivalent to that of the currently available inactivated virus vaccines, and will need to provide a wide spectrum of protection against antigenic variants.

Attempts to design a defined subunit vaccine for FMDV began with disruption of the virus particle and identification of its constituent proteins as shown in FIG. 1. This results in a considerable loss of immunogenic activity in comparison to intact inactivated virus particles (Brown, 1989). However, it was found that the separated capsid protein now uniformly designated as VP1 had, by itself, the capacity to elicit neutralizing antibodies and immunity from challenge in cattle and swine, although the activity was subtype specific and many orders of magnitude lower than that of the intact inactivated virus. None of the other virus proteins evoked neutralizing activity (Laporte et al., C R Acad Sci Paris, 1973; 276:3399–3401 and, Bachrach et al., J. Immunol., 1975; 115:1636–1641).

The neutralizing activity of VP1 focused attention on this protein and initially it was seriously considered as a candidate for a genetically engineered subunit vaccine (Kleid et al., Science, 1981; 214:1125–1129). It soon became clear that the immunogenicity of recombinant VP1 was insufficient to protect animals (Brown, 1989; Brown, 1992). Nevertheless, this work led to the discovery of immunogenic determinants on VP1, and the possibility of more potent site-specific subunit vaccines based on synthetic peptides.

VP1 was mapped for immunogenic sites by Strohmaier et al. (3 Gen Virol, 1982; 59:295–306) who tested VP1 cleavage products generated by cyanogen bromide and proteolytic digestion; by Bittle and Lemer (WO 83/03547) who tested synthetic peptides whose amino acid sequences corresponded to regions of highest variability, by Acharya et al. (Nature, 1989, 337:709–711) who identified surface-exposed sites on FMDV by X-ray crystallography, and by Pfaff et al. (EMBO J, 1982; 7:869–874) who selected a peptide that elicits neutralizing antibody by prediction of a prominent amphipathic helical conformation in VP1. All four approaches converged on a loop region of VP1 spanning residues 137–160 as bearing a determinant that elicits neutralizing antibodies.

Serotype-specific peptides corresponding to the 141–160 region of VP1, also termed the "G-H loop", from FMDV isolates belonging to all seven serotypes have now been shown to elicit protective levels of neutralizing antibody in guinea pigs (Francis et al., Immunology, 1990; 69:171–176). Clearly this region contains a dominant immunogenic site which also carries the serotype specificity of the virus. The initial observations of immunogenicity for these 141–160 VP1 peptides was accomplished using synthetic peptides conjugated to carrier protein KLH (keyhole limpet hemocyanin), a procedure which negates the advantage of manufacturing a well-defined synthetic immunogen. However, the development of VP1 synthetic immunogens was advanced by DiMarchi and Brook (U.S. Pat. No. 4,732,971) who showed that two VP1 sequences from a subtype O isolate, joined in a 200–213 Pro-Pro-Ser-141–158-Pro-Cys-Gly chimeric construct, elicited antibody levels which protected cattle against challenge. Nevertheless, the efficacy of this effect was limited by the low immunogenicity of the peptide immunogen. High doses of 1–5 mg were required to achieve protection from homotypic intradermalingual challenge and one of three animals receiving the 5 mg dose was not protected. Practical application demands that a vaccine formulation provide complete protection from both homotypic and heterotypic challenge with smaller amounts of peptide immunogen.

An important element for an effective peptide vaccine for FMDV is the selection of a precise sequence from the G-H loop domain of VP1 that is optimal for presentation of the B cell epitope that is responsible for eliciting neutralizing antibodies. The frame for the optimal presentation of a domain by a peptide can be affected by a shift as small as a single amino acid position (Moore, Chapter 2 in *Synthetic Peptides A User's Guide*, ed Grant, WH Freeman and Company: New York, 1992, pp 63–67). Preferred synthetic immunogens comprising the immunodominant G-H loop neutralizing determinant have been disclosed including residues 141–160 (WO 83/0357; Francis et al, 1990), 141–158 (U.S. Pat. No. 4,732,971), 142–158 (Parry et al. WO 91/03255), 137–168 (Morgan and Moore, Am J Vet Res, 1990; 51: 40–45), 138–156 (Taboga et al, J Virol, 1997; 71:2602–2614), and any contiguous sequence of 20 amino acids selected from 130–160 (WO 83/03547). Clearly, there is no consensus on a unique segment of VP1 that is optimal for presentation of the G-H loop VP1 neutralizing site.

In addition, the limited variety of B cell epitopes in prior peptide vaccines have not been adequate to stimulate the broadly -reactive neutralizing antibodies needed for protection against the highly variable FMDV. Up to the present time, only antibodies with relatively limited specificities have been elicited and there is a further restriction on the value of even these limited specificities due to the occurrence over time of point mutations giving rise to escape mutants (Taboga et al, 1997). Alternative methods are needed to provide a peptide vaccine with immunogenicity that is sufficiently broad to overcome antigenic variation among multiple strains and temporal variation caused by the emergence of escape mutants.

Another important factor affecting immunogenicity of a synthetic peptide for an FMDV vaccine is presentation to the immune system of a T-helper cell epitope appropriate for the host. Short synthetic peptides can realize their potential as vaccines only if they contain domains that react with helper T-cell receptors and Class II MHC molecules, in addition to antibody binding sites (Babbitt et al., Nature, 1985; 317:359–361). The 141–160 VP1 peptide alone is somewhat immunogenic for guinea pigs and mice, pointing to the presence of T-cell epitopes in the sequence which are appropriate for those species. In contrast to results with those laboratory animals, vaccine trials in cattle and swine suggest that immune responsiveness to the T-cell epitopes of this VP1 domain is too variable for adequate protection among individuals of these economically significant outbred species (Rodriguez et al, Virology, 1994; 205:24–33; and, Taboga et al, J Virol, 1997; 71:2606–2614). Recently, other synthetic peptides corresponding to regions of FMDV structural proteins have been identified which act as T-helper cell sites. A peptide corresponding to VP1 amino acids 21–40 was found to provide T cell help in cattle to the VP1 neutralizing loop sequence (Collen et al., J Immunol, 1991; 146:749–755); however, the presence of this T cell epitope was not sufficient to provide consistent protection in cattle (Taboga et al, 1997). There is still no information regarding the selection of adequate T helper cell determinants nor is the optimal orientation of B- and T-cell epitopes in FMDV peptide vaccines known.

There remains a need for a synthetic peptide-based vaccine for FMDV that is of potency and broadness superior to the classical vaccines. The prior art peptides discussed above do not adequately address this need.

It is an object of the present invention to provide a synthetic peptide FMD vaccine that meets this need. The methods used to attain this goal are:

1. an effective procedure for the identification of high affinity epitopes,
2. the means to represent an enlarged repertoire of B cell and T cell epitopes with a small number of peptide syntheses through combinatorial chemistry,
3. the means to augment the immunogenicity of a B cell target epitope by combining it with a potent T helper cell (Th) epitope and accommodating the Th epitope to the variable immune responsiveness of a population, and 4. the stabilization of desirable conformational features by the introduction of cyclic constraints.

Synthetic peptides have been used for "epitope mapping" to identify immunodominant determinants or epitopes on the surface of proteins, for the development of new vaccines, and diagnostics. Epitope mapping employs a series of overlapping peptides corresponding to regions on the protein of interest to identify sites which participate in antibody-immunogenic determinant interaction. Most commonly, epitope mapping employs peptides of relatively short length to precisely detect linear determinants. A fast method of epitope mapping known as "PEPSCAN" is based on the simultaneous synthesis of hundreds of overlapping peptides, of lengths of 8 to 14 amino acids, coupled to solid supports. The coupled peptides are tested for their ability to bind antibodies. This approach is effective in localizing linear determinants, but the immunodominant epitopes needed for vaccine development are usually high affinity discontinuous epitopes and are difficult to define by the PEPSCAN method (Meloen et al., Ann Biol Clin, 1991; 49:231–242).

An alternative method relies on a set of nested and overlapping peptides of multiple lengths ranging from 15 to 60 residues. These longer peptides are synthesized by a laborious series of independent solid-phase peptide syntheses, rather than by the rapid and simultaneous PEPSCAN syntheses. The resulting set of nested and overlapping peptides can then be used in antibody binding studies and experimental immunizations to identify long peptides which best present immunodominant determinants, including simple discontinuous epitopes. This method is exemplified by the studies of Wang for the mapping of immunodominant sites from HTLV I/II (U.S. Pat. No. 5,476,765) and HCV (U.S. Pat. No. 5,106,726); and it was used for the selection of a precise position on the gp 120 sequence for optimum presentation of an HIV neutralizing epitope (Wang et al., Science, 1991; 254:285–288).

Combinatorial peptide libraries have been designed to cover the broad range of sequences embraced by geographical or population differences and temporal variation of hypervariable antigens and to circumvent the limited capacity of individual peptide immunogens. For example, a particular peptide antigen may be designed to contain multiple positional substitutions organized around a structural framework of invariant residues. This combination maintains the conformation of an immunodominant site and accommodates present and anticipated antigenic variation. Such combinatorial peptides, corresponding to hypervariable immunodominant sites of HIV and HCV, have been described as "mixotopes" by Gras-Masse et al. (Peptide Research, 1992; 5:211–216), and as "structured synthetic antigen library" or "SSAL" by Wang et al. (WO 95/11998).

A "structured synthetic antigen library" or SSAL is composed of an ordered set of related peptide sequences embedded within a larger invariant structural framework capable of maintaining the antigenicity, diagnostic value or therapeutic bioactivity of that site.

Equation 1 provides a representation of the SSAL amino acid sequence.

$$AA_{1j}AA_{2j} \ldots AA_{ij} \ldots AA_{xj} \quad \text{(Eqn. 1)}$$

The sequence $AA_{1j}$ to $AA_{xj}$ represents the amino acid sequence, from the N-terminus to the C-terminus, of the peptides in the SSAL. Each peptide in the library has length x, and x is constant for each library. At each amino acid position i, j varies from 1 to n, where n represents the number of different amino acids known (or desired) at the ith position. The deliberate introduction or natural occurrence of gaps or insertions, e.g. those in the VP1 sequence alignments in Table 1, is accommodated by the synthesis of separate SSALs with different values of x.

Equation 2 is a mathematical representation of the sum of the relative ratios of amino acids at a given variable position i in the SSAL sequence.

$$\sum_{j=1}^{n} [AA_{ij}] = 1 \quad \text{(Eqn. 2)}$$

Equation 2 states that at each position i, the sum of the molar fractions of the n individual amino acids is unity. The molar fraction of the jth amino acid at position i, $[AA_{ij}]$, is selected by the practitioner, based upon (1) the prevalence of $AA_{ij}$ among the subtype strains of an FMDV serotype as found in nature, and optionally (2) the desire to include similar amino acids in order to anticipate escape mutants. The amino acids $AA_{ij}$ will ordinarily be selected from the naturally occurring amino acids, but may include modified amino acids such as ornithine and norleucine and unnatural amino acids such as D-amino acids. By following these formulas, all the variant sequences of an SSAL having length x can be prepared simultaneously in a single synthesis.

The sequence of the SSAL is determined by aligning the primary amino acid sequences of a related family of antigens, and identifying the invariant and variant loci within the alignment. The invariant loci generally represent the structural framework of the SSAL. The degeneracy within the SSAL is determined by the loci within the alignment that harbor different amino acid residues relative to an arbitrary prototype sequence. After determining which amino acids are to be at each invariant position, the degree of degeneracy for the variable positions in the SSAL library is determined from the number of variants that present each alternative amino acid. The SSAL is then synthesized with single amino acids at the invariant positions and with the requisite degeneracies at the variant positions.

The relative ratios of the amino acid residues at the variant positions may be set equal to one another, or they may be represented in unequal proportions. In a preferred embodiment, the amino acid ratios at one or more variant positions are set to reflect the relative prevalence of each amino acid found in the native sequences. The SSAL libraries exemplified in FIGS. 2 and 4 represent such preferred embodiments, wherein the subscripts represent the relative amounts of the individual residues at each variable position in the SSAL. It should be noted that a large fraction of the peptides present in an SSAL may represent combinations of variable amino acids which have not yet been observed in nature. This feature of an SSAL increases the degree to which protection against FMDV infection by new, emerging strains of FMDV is conferred by the peptide compositions of this invention.

Thus, in a simple manner, the specific amino acids, and optionally their frequency of appearance at each position within the SSAL, are defined by the primary sequences of the different antigens that are used in the alignment. In anticipation of escape mutants, amino acids not known to exist in nature at a variant locus within the aligned epitopes can optionally be incorporated into the library. For example, several or all residues of a specific class of amino acids (e.g. hydrophobic, charged, neutral or polar) can be incorporated at any variable locus. The class of amino acids incorporated at a specific locus can be determined by the predominant type of amino acid found at that variant locus within the antigen alignment (WO 95/11998).

Epitopes termed "promiscuous Th" evoke efficient T cell help, and can be combined with B cell epitopes that by themselves are poorly immunogenic to generate potent peptide immunogens. Well-designed promiscuous Th/B cell epitope chimeric peptides are capable of eliciting Th responses and resultant antibody responses in most members of a genetically diverse population expressing diverse MHC haplotypes. Promiscuous Th can be provided by specific sequences derived from potent immunogens of viral and bacterial origin, including measles virus F protein, hepatitis B virus surface antigen, and *Chlamydia trachomatis* major outer membrane protein. Many known promiscuous Th have been shown to be effective in potentiating a poorly immunogenic peptide corresponding to the decapeptide hormone LHRH (U.S. Pat. No. 5,759,551).

Potent Th epitopes range in size from about 15 to about 50 amino acid residues in length (U.S. Pat. No. 5,759,5 51), and often share common structural features and may contain specific landmark sequences. For example, a common feature is amphipathic helices, which are alpha-helical structures with hydrophobic amino acid residues dominating one face of the helix and with charged and polar residues dominating the surrounding faces (Cease et al., Proc Natl Acad Sci USA, 1987; 84:4249–4253). Th epitopes frequently contain additional primary amino acid patterns such as a Gly or charged residue followed by two to three -hydrophobic residues, followed in turn by a charged or polar residue. This pattern defines what are called Rothbard sequences. Also, Th epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single Th epitope (Partidos et al., 3 Gen Virol, 1991; 72:1293–1299). Most, if not all, of the promiscuous T cell epitopes fit at least one of the periodicities described above. These features may be incorporated into the designs of idealized artificial Th sites, including SSAL Th epitopes that can provide degeneracy at positions associated with recognition of diverse MHC molecules and retain invariant positions. Lists of variable positions and preferred amino acids are available for MHC-binding motifs (Meister et al., Vaccine, 1995; 13:581–591). For example, the degenerate Th epitope described in WO 95/11998 as "SSAL1TH1" was modeled after a promiscuous epitope taken from the F protein of measles virus (Partidos et al., 1991). SSAL1TH1 (WO 95/11998) was designed to be used in tandem with an LHRH target peptide. Like the measles epitope, SSAL1ITH1 follows the Rothbard sequence and the 1, 4, 5, 8 rule.

(See, e.g., positions 6, 9, 10 and 13 in SSAL1TH1):

feature is to enlarge the range of immune responsiveness to an artificial Th (WO 95/11998). All variants within such an SSAL are produced simultaneously in a single solid-phase peptide synthesis in tandem with the targeted B cell epitope and other sequences.

Peptide immunogens are generally more flexible than proteins and tend not to retain any preferred structure. Therefore it can be useful to stabilize a peptide immunogen by the introduction of cyclic constraints. A correctly cyclized peptide immunogen can mimic and preserve the conformation of the targeted epitope and thereby evoke antibodies with -reactivities on that site on the authentic molecule (Moore, Chapter 2 in *Synthetic Peptides A User's Guide*, ed Grant, WH Freeman and Company: New York, 1992, pp 63–67). This has been accomplished for a peptide that represents the FMDV immunodominant VP1 loop domain, by adding cysteine residues at both the amino and carboxy termini and cyclization by oxidation of the two cysteine residues (WO 83/03547). However, there remains a need for more effective peptide analogs of the VP1 loop domain.

Peptides having more immunologically effective conformations are provided by the present invention. These have been obtained by discovering those positions for the cysteine residues that result in a more accurate imitation of the native epitope (Valero et al. Biomedical Peptides, Proteins and Nucleic Acids, 1995; 1:133–140).

SUMMARY OF THE INVENTION

The present invention provides peptide immunogens that have been designed with the peptide technologies and peptide design elements discussed above, i.e., precise epitope mapping, SSAL library peptides, design of potent Th epitopes, and cyclic constraint. These peptide immunogens are the basis for effective synthetic FMDV vaccines. Such peptides are preferred for their presentation of the VP1 neutralizing site with optimized positioning and conformational constraint, for their presentation of the broad range of sequences necessitated by FMDV serotype variation, and for their broadly reactive Th responsiveness.

The present invention further provides for the use of such peptide compositions as an immunogen, with each peptide contained therein comprising a target antigenic site derived from the VP1 capsid protein of Foot-and-Mouth Disease Virus (FMDV), preferably with said antigenic site covalently linked to a helper T cell epitope and, optionally, other immunostimulatory sequences, preferably by conventional peptide bond(s) through direct synthesis, for the prevention of FMDV infection and eradication of FMD.

More particularly, the present invention relates to the use of such peptide composition as an immunogen to elicit the production in animals including swine, cattle, sheep, goats,

```
1               5                    10              15
Asp-Leu-Ser-Asp-Leu-Lys-Gly-Leu-Leu-Leu-His-Lys-Leu-Asp-Gly-Leu-
Glu Ile     Glu Ile Arg     Ile Ile Ile     Arg Ile Glu     Ile
    Val         Val             Val Val Val         Val         Val
    Phe         Phe             Phe Phe Phe         Phe         Phe
```

Charged residues Glu or Asp are added at position 1 to increase the charge surrounding the hydrophobic face of the Th. The hydrophobic face of the amphipathic helix is then maintained by hydrophobic residues at 2, 5, 8, 9, 10, 13 and 16, with variability at 2, 5, 8, 9, 10, 13 and 16 to provide a facade with the capability of binding to a wide range of MHC restriction elements. The net effect of the SSAL and FMDV-susceptible wild species, of high titer polyclonal antibodies that can effectively neutralize, in vitro, multiple strains or serotypes of FMDV, and to the use of such composition as a vaccine to effectively prevent, and/or reduce the incidence of FMDV infection regardless of its antigenic diversity, and thus cause the eradication of FMD.

The present invention also relates to the peptides used in the compositions, and to immunoassays and/or diagnostic kits containing one or more of these peptides, or segments thereof.

The target antigenic sites of the present invention were selected through epitope mapping based on the amino acid sequence information derived from the VP1 protein of FMDV $A_{12}$ strain and represent a frame for the optimal presentation of the neutralizing determinant on the FMDV VP1 protein, amino acids 134 to 168. These residues appear as amino acids "134–169" in Table 1 (SEQ ID NO:1), due to the presence of a gap at position 142 which is introduced for purposes of alignment. They will be referred to in the text as amino acids 134–169 as a matter of convenience, but it will be understood that residues 134–168 (SEQ ID NO:1) is the actual fragment under discussion.

The target antigenic sites of the present invention are preferably modified from that of the naturally occurring FMDV VP1 sequences of the G-H loop region by the substitution of cysteine for two native amino acids, and the formation of a disulfide bond between these cysteines so as to produce a cyclic structure having from about 20 to about 25 residues between the cysteines (e.g., SEQ ID NO:2). Corresponding target sites for VP1 of other serotypes can be derived from the homologous G-H loop region segment of the relevant serotypes.

The present invention further provides FMDV VP1 target antigenic sites with consensus sequences according to the optimized frame of SEQ ID NO: 1 with highly variable positions embedded within an invariant structural framework, wherein the most frequently employed amino acid for each of the highly variable positions is represented, as determined by analyses of the VP1 sequences from a group of FMDV subtypes related to a specific FMDV serotype.

The present invention further provides structured synthetic antigen libraries (or SSALs) according to the optimized target antigen peptide frame of SEQ ID NO: 1, wherein each SSAL is composed of an ordered set of related peptides produced simultaneously in a single peptide synthesis having sequences imposed upon an invariant structural framework capable of maintaining the antigenicity of the target antigenic peptide.

In addition, the target site of the peptides and their analogs of the present invention are rendered immunogenic via covalent linkage in tandem combinations to synthetic immunostimulatory elements including an immunostimulatory invasin peptide (Inv) taken from Yersinia (SEQ ID NO.:22), promiscuous Th epitopes derived from foreign pathogens; autologous Th epitopes derived from FMDV proteins (e.g., SEQ ID NO:24, Table 5), artificial Th epitopes (e.g., SEQ ID NOS:25 and 26, Table 6) and others through direct synthesis. Peptides of the invention may be represented by the formulas:

$(A)_n$-(FMDV antigen)-$(B)_o$-$(Th)_m$-X or $(A)_n$-$(Th)_m$-$(B)_o$-(FMDV antigen)-X or (FMDV antigen)-$(B)_o$-$(Th)_m$-$(A)_n$-X or $(Th)_m$-$(B)_o$-(FMDV antigen)-$(A)_n$-X wherein each A is independently an amino acid or a general immunostimulatory sequence;

each B is independently an amino acid or a chemical linker as further defined below;

each Th is independently a sequence of amino acids that constitutes a helper T cell epitope, or an immune enhancing analog or segment thereof;

"FMDV antigen" is a synthetic peptide antigen as defined further below;

X is an amino acid α-COOH or α-CONH$_2$;

n is from 0 to about 10;

m is from 1 to about 4; and o is from 0 to about 10.

Also provided are adjuvants and/or delivery vehicles and other ingredients routinely incorporated with vaccine formulations, and instructions for dosage such that polyclonal antibodies directed against the FMDV VP1 target antigenic site are generated.

The present invention relates to the use of peptide compositions as an immunogen to elicit the production in animals including swine, cattle, sheep, goats, and FMDV-susceptible wild species, of high titer polyclonal antibodies. The FMDV protection mechanism, mediated by the antibodies and induced by the peptide compositions of the present invention, will effectively neutralize, in vitro, multiple strains of FMDV regardless of serotype or subtype, and thus lead to protective immunity from FMDV infection and assist in the eradication of FMD.

BRIEF DESCRIPTION OF THE DRAWINGS

FIG. 2A depicts the amino acid composition of Structured Synthetic Antigen Library "A SSAL(1)(COMPLETE) (134–169)". Subscripts represent the relative amounts of each amino acid at the corresponding position.

FIG. 2B depicts the amino acid composition of Structured Synthetic Antigen Library "A SSAL(1)(COMPLETE)[134(N→C)-158(Q→C)-169]."

FIG. 3A depicts the amino acid composition of Structured Synthetic Antigen Library "A SSAL(2)(COMPLETE) (134–169)".

FIG. 3B depicts the amino acid composition of Structured Synthetic Antigen Library "A SSAL(2)(COMPLETE)[134(N→C)-158(Q→C)-169]."

FIG. 4A depicts the amino acid composition of Structured Synthetic Antigen Library "O SSAL(COMPLETE) (134–169)".

FIG. 4B depicts the amino acid composition of Structured Synthetic Antigen Library "O SSAL(COMPLETE) [134–158(T→C)-169]."

DETAILED DESCRIPTION OF THE INVENTION

Figure 1:
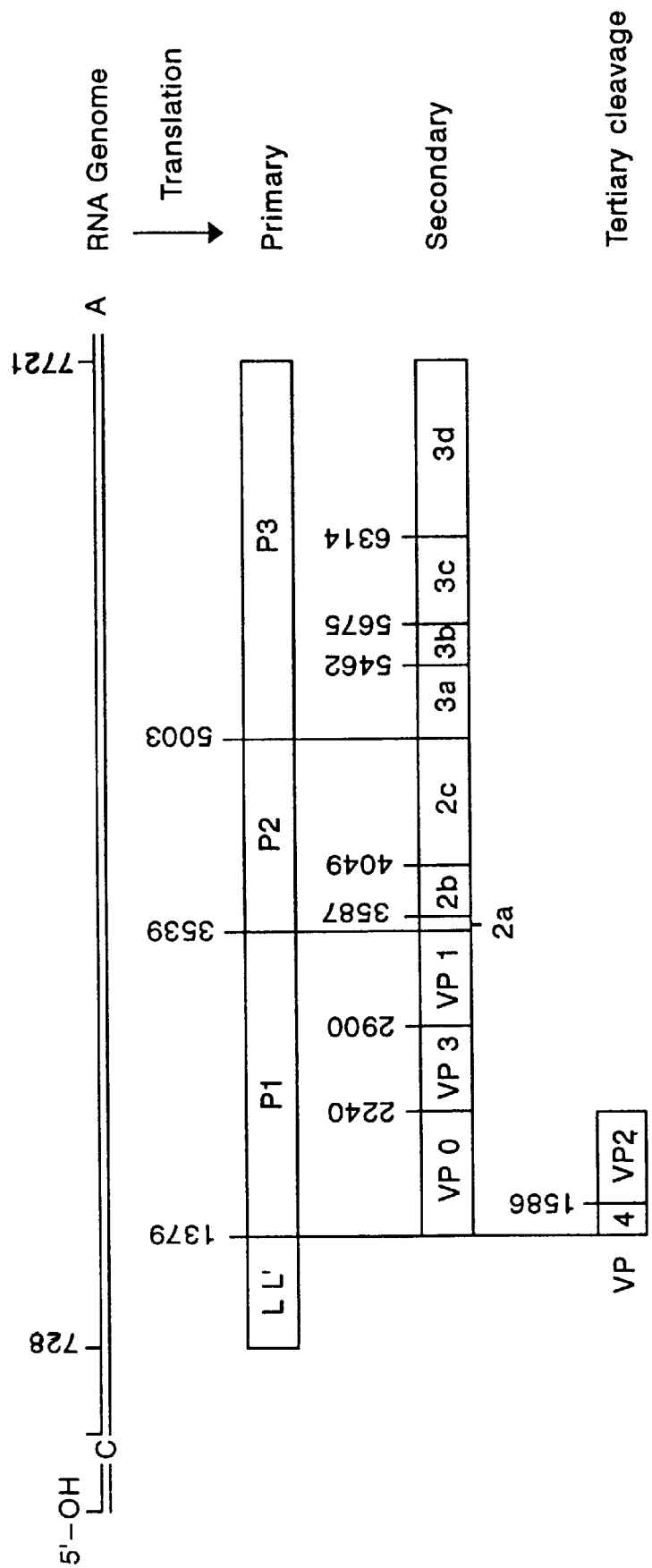
FIG. 1 depicts the organization of the FMDV genome, the processing pathway by which the translation products are cleaved into viral protein, and the nomenclature for the capsid and non-structural proteins.

The present invention relates to the use of a peptide composition as an immunogen, said composition comprising one or preferably more peptides, with each peptide contained therein comprising a target antigenic peptide derived from the VP1 capsid protein of Foot-and-Mouth Disease Virus (FMDV), said antigenic peptide preferably being covalently linked to a helper T cell epitope and optionally to other immunostimulatory sequences. The covalent linkage is preferably by peptide bond(s) generated through direct synthesis.

The peptide compositions are useful for the prevention of FMDV infection in animals, and are expected to assist in the eradication of FMD. More particularly, the present invention relates to the use of such peptide compositions as immunogens to elicit the production in animals, including swine, cattle, sheep, goats and susceptible wild species, of high titer polyclonal antibodies that can effectively neutralize, in vitro, multiple strains or serotypes of FMDV, and to the use of such compositions as a vaccine to prevent FMDV infection regardless of serotypes, and thus effect the eradication of FMD.

The present invention also relates to the peptides used in the compositions, and to immunoassays and/or diagnostic kits containing one or more of these peptides, or segments thereof. Immunoassays and/or diagnostic kits containing one or more of these peptides, or segments thereof, will be useful to identify vaccine-induced antibodies and antibodies induced by infection, and thus can be used to screen for the presence of FMDV infection and/or to monitor the effectiveness of a vaccination program.

The invention provides a method of diagnosing FMDV infection in a mammal, comprising the steps of:

(a) attaching a peptide according to claim 1 to a solid support, (b) exposing said peptide attached to said solid support to a sample containing antibodies from said mammal, under conditions conducive to binding of the antibody to the peptide, and (c) detecting the presence of antibodies bound to said peptide attached to said solid support.

The targeted antigenic sequence comprising the principal neutralizing determinant of FMDV VP1 (the G-H loop) was optimized based on consideration of potential looped conformation and surface exposure for residues of the G-H loop, as deduced from the three-dimensional structure of FMDV VP1 made available by the Brookhaven National Laboratory at internet address http://www.pdb.bnl.gov/pdb.bin/pdbids and reported in Acharya et al., Nature 337:709–711, 1989. Candidate positions for cyclization were incorporated into the design of peptide constructs and modified and non-modified sequences were synthesized as immunogens by covalent attachment to promiscuous Th epitopes with or without other immunostimulatory elements, by continuous synthesis. The modified peptide constructs were synthesized as cyclic peptides, with the incorporation of specific disulfide bonds, so as to stabilize the mobile peptides into potentially more biologically relevant conformations. Synthetic constructs comprising VP1 antigenic sites of relevant immunogenicity were identified by the preparation of hyperimmune sera and testing of the sera for their potency in FMDV neutralization assays. Specifically, the target antigenic sites of the present invention were selected through epitope mapping based on the amino acid sequence of the VP1 protein of FMDV strain $A_{12}$ (Example 2).

The frame for the target antigen peptides, AA134–169 shown in Table 1 by SEQ ID NO: 1 was found to be optimum for immunogenic presentation of the G-H loop neutralizing determinant on FMDV VP1. The target antigenic sites of the antigenic peptides can be modified from that of the naturally occurring FMDV VP1 sequences by the substitution for the native asparagine at position 134 and glutamine at position 157 by cysteines and the formation of a disulfide bond between the substituent cysteines so as to produce a cyclic structure (SEQ ID NO:2). Said cyclic structures also comprise 1 to 13 additional amino acids taken from either termini of the 134–157 segment of VP1 provided that the single disulfide looped structure is preserved as shown in Table 1 by SEQ ID NO:3. As an example of a target antigenic peptide of the present invention there is provided a 3'target site for FMDV VP1 having the following sequence (cysteine substituents are indicated by boldface):

Cys-Lys-Tyr-Ser-Ala-Ser-Gly-Ser-Gly-Val-Arg-Gly-Asp-Phe-Gly-Ser-Leu-Ala-Pro-Arg-Val-Ala-Arg-Cys-Leu-Pro-Ala-Ser-Phe-Asn-Tyr-Gly-Ala-Ile-Lys (SEQ ID NO.:2)

Likewise, corresponding target sites for VP1 of other serotypes can be derived from the homologous segment of the relevant serotypes. For example, substitution peptide analogs can be prepared according to the corresponding sequences from FMDV serotypes O and Asia through sequence alignment as shown in Table 1 having respective sequences of:

Cys-Lys-Tyr-Ser-Ser-Lys-Ala-Val-Pro-Asn-Val-Arg-Gly-Asp-Leu-Asn-Val-Leu-Glu-Gln-Lys-Ala-Ala-Arg-Cys-Leu-Pro-Thr-Ser-Phe-Asn-Tyr-Gly-Ala-Ile-Lys (SEQ ID NO:5)

and

Cys-Pro-Tyr-Gly-Glu-Thr-Thr-Ser-Arg-Arg-Gly-Asp-Met-Ala-Ala-Leu-Ala-Gln-Arg-Leu-Ser-Ala-Cys-Leu-Pro-Thr-Ser-Phe-Asn-Tyr-Gly-Ala-Val-Lys (SEQ ID NO:7)

The present invention further provides FMDV VP1 target antigenic peptides, cyclized and linear, with consensus sequences according to the optimized frame of SEQ ID NO: 1 (AA134–169) with highly variable positions imposed upon an invariant structural framework wherein the most frequently employed amino acid for each of the highly variable positions is represented, as determined by analyses of the VP1 sequences from a group of viruses related to a specific FMDV serotype. As examples of such consensus sequences of the present invention, there are provided six consensus sequences derived from FMDV variants of serotype A (SEQ ID NOS:8,9), serotype O (SEQ ID NOS:10,11) and serotype Asia (SEQ ID NOS:12,13) as shown Table 1.

Figures 3A, 3B:
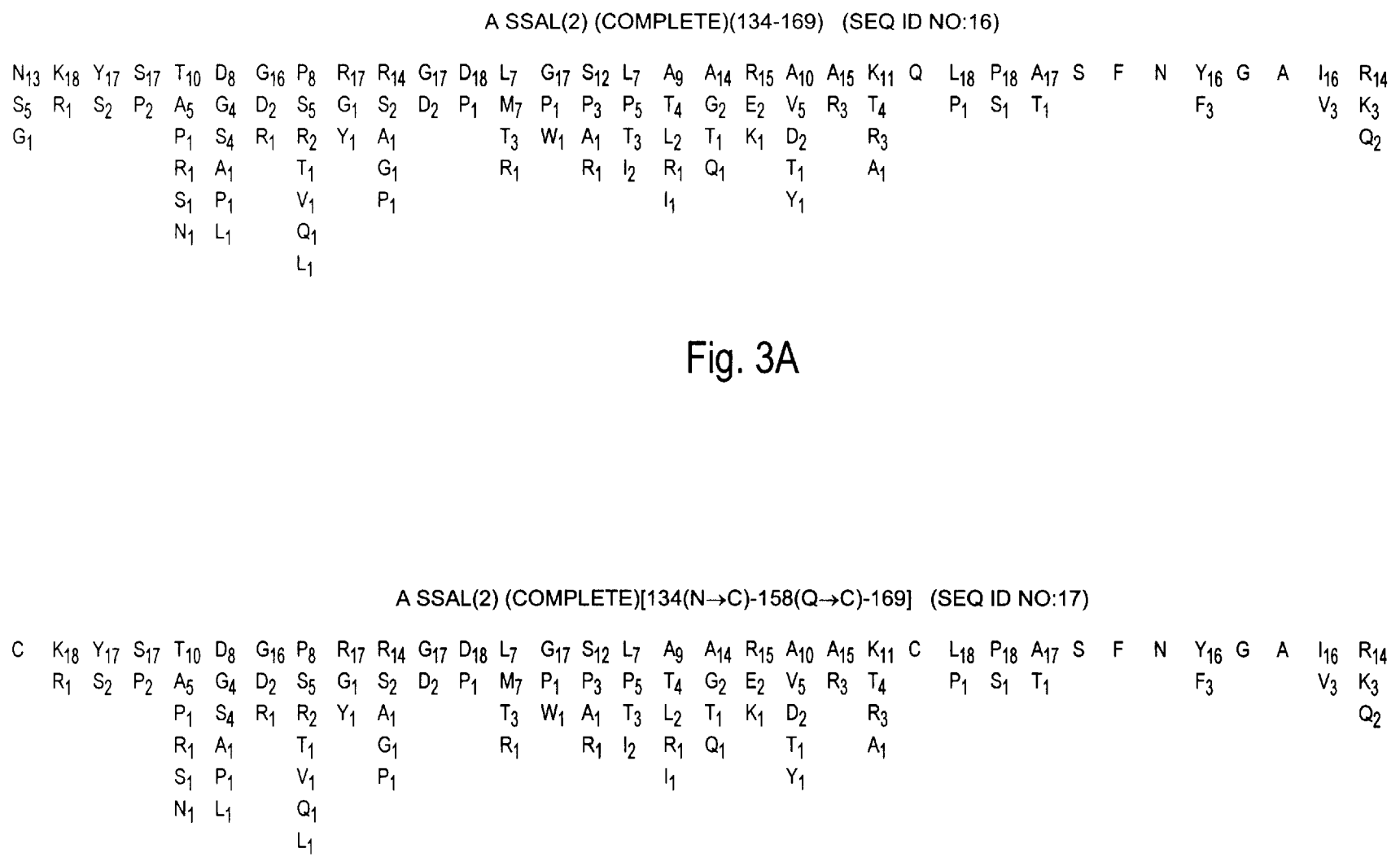
Figures 4A, 4B:
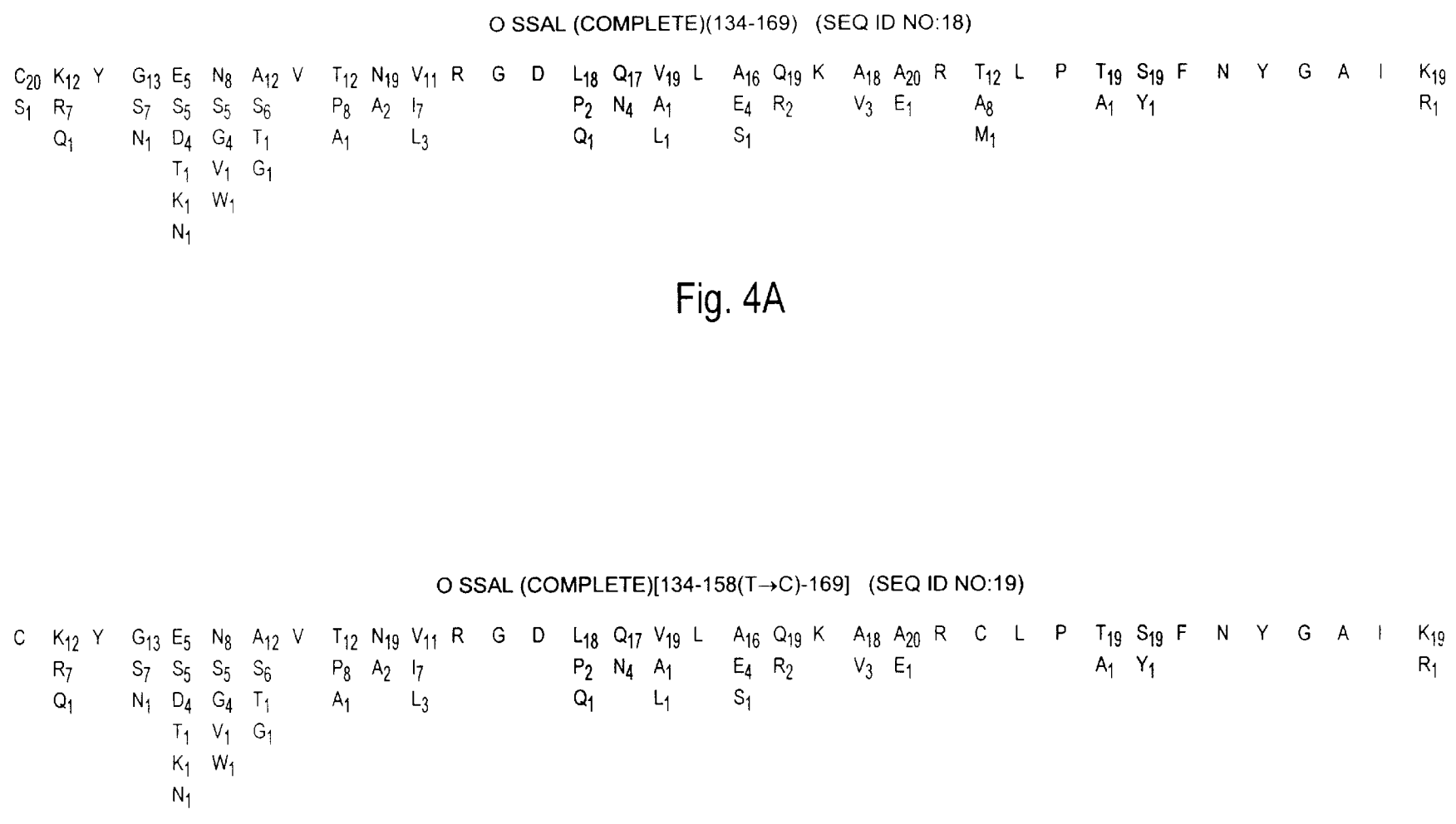

The present invention further provides structured synthetic antigen libraries (or SSALs), cyclized and linear, according to the optimized target antigen peptide frame of SEQ ID NO: 1, wherein each SSAL is composed of an ordered set of related peptides produced simultaneously in a single peptide synthesis having sequences imposed upon an invariant structural framework capable of maintaining the antigenicity of the target antigenic peptide. As examples of such SSALs of the present invention, there are provided nine SSALs with the composite sequences derived from FMDV subtype groups of serotype A (SEQ NOS: ID 14–17, FIGS. 2A, 2B, 3A, 3B), serotype O (SEQ ID NOS:18,19, FIGS. 4A, 4B) and serotype Asia (SEQ ID NOS:20,21,35) as compiled in Tables 2, 3, and 4 respectively.

The target VP1 sites are short peptide sequences. When synthesized by themselves as peptides of the invention such peptides are usually weak immunogens. These short peptides can be immunopotentiated by chemical linkage to promiscuous Th epitopes derived from foreign pathogens including but not limited to, as examples, hepatitis B surface and core antigen helper T cell epitopes (HBsTh and HBcTh), pertussis toxin helper T cell epitopes (PT Th), tetanus toxin helper T cell epitopes (TT Th), measles virus F protein helper T cell epitopes (MVF Th), *Chlamydia trachomatis* major outer membrane protein helper T cell epitopes (CT Th), diphtheria toxin helper T cell epitopes (DT Th), *Plasmodium falciparum* circumsporozoite helper T cell epitopes (PF Th), *Schistosoma mansoni* triose phosphate isomerase helper T cell epitopes (SM Th), *Escherichia coli* TraT helper T cell epitopes (TraT Th). The pathogen-derived Th selected here as representative examples of promiscuous Th were listed as SEQ ID NOS:2–9 and 42–52 in U.S. Pat. No. 5,759,551; as Chlamydia helper site P11 in Stagg et al., *Immunology*, 1993; 79;1–9; and as HBc peptide 50–69 in Ferrari et al., *J Clin Invest*, 1991; 88:214–222, and are incorporated herein by reference. Promiscuous Th also include autologous Th epitopes derived from FMDV proteins (Table 5, e.g., SEQ ID NO:24) incorporated herein by reference, or designed artificial Th epitopes as shown in Table 6, e.g., SEQ ID NOS:25, 26, 36 ,37, and 38.

The immunogens of the invention are all of site-specific immunoreactivity to provide precise targeting of the principal neutralizing determinant of FMDV. Specific examples are provided as embodiments of peptides of the invention, e.g., SEQ ID NOS: 2,11. Further examples are provided as preferred peptides of the invention which provide for the linkage of synthetic immunostimulatory elements to the FMDV VP1 antigenic sites (e.g., SEQ ID NOS:27–34 in Tables 7–10) such that broadly reactive potent neutralizing antibodies are generated, in a genetically diverse host population, against the targeted site on the FMDV VP1 protein. These anti-VP1 antibodies lead to effective neutralization of FMDV and thus protection from FMDV infection.

For active immunization, the term "immunogen" referred to herein relates to a peptide composition which is capable of inducing antibodies against a G-H loop site present on the VP1 protein of FMDV, leading to effective neutralization of FMDV of multiple serotypes and thus prevention of FMDV infection. The peptide composition of the present invention preferably includes synthetic peptides which contain promiscuous helper T cell epitopes (Th epitopes) and optionally other immunostimulatory elements. The Th peptides are covalently attached to the FMDV VP1 target antigenic site (e.g., SEQ ID NOS:1–21,35), with a spacer (e.g., Gly— Gly), so as to be adjacent to either the N- or C-terminus of the target antigenic site, in order to evoke effective antibody responses. The immunogen may also comprise general immunostimulatory amino acid sequences, for example, corresponding to a domain of an invasin protein from the bacteria Yersinia spp (Brett et al., *Eur J Immunol*, 1993, 23:1608–1614) (SEQ ID NO:22). When present, the general immunostimulatory domain may include a spacer for attachment through a peptide.

The peptides of this invention can be represented by the formulas:

$(A)_n$-(FMDV antigen)-$(B)_o$-$(Th)_m$-X or $(A)_n$-$(Th)_m$-$(B)_o$-(FMDV antigen)-X or (FMDV antigen)-$(B)_o$-$(Th)_m$-$(A)_n$-X or $(Th)_m$-$(B)_o$-(FMDV antigen)-$(A)_n$-X wherein each A is independently an amino acid or a general immunostimulatory sequence;

each B is independently chosen from the group consisting of amino acids, —NHCH(X)CH$_2$SCH$_2$CO—, —NHCH(X)CH$_2$SCH$_2$CO(ε-N)Lys-, —NHCH(X)CH$_2$S-succinimidyl(ε-N)Lys-, and —NHCH(X)CH$_2$S-(succinimidyl)-;

each Th is independently a sequence of amino acids that constitutes a helper T cell epitope, or an immune enhancing analog or segment thereof;

"FMDV antigen" is a synthetic peptide antigen as defined further below;

X is an amino acid α-COOH or α-CONH$_2$;

n is from 0 to about 10;

m is from 1 to about 4; and o is from 0 to about 10.

The peptide immunogen of the present invention comprises from about 35 to about 100 amino acid residues, preferably from about 45 to about 90 amino acid residues and more preferably from about 50 to about 75 amino acid residues.

When A is an amino acid, it can be any non-naturally occurring or any naturally occurring amino acid. Non-naturally occurring amino acids include, but are not limited to, β-alanine, ornithine, norleucine, norvaline, hydroxyproline, thyroxine, γ-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Moreover, when m is greater than one, and two or more of the A groups are amino acids, then each amino acid may be independently the same or different.

When A is an invasin domain, it is an immune stimulatory epitope from the invasin protein of a Yersinia species. This immune stimulatory property results from the capability of this invasin domain to interact with the BI integrin molecules present on T cells, particularly activated immune or memory T cells. The specific sequence for an invasin domain found to interact with the β1 integrins has been described by Brett et al. (Eur J Immunol, 1993). A preferred embodiment of the invasin domain (Inv) for linkage to a promiscuous Th epitope has been previously described in U.S. Pat. No. 5,759,551, which is incorporated herein by reference. The preferred Inv domain has the sequence Thr-Ala-Lys-Ser-Lys-Lys-Phe-Pro-Ser-Tyr-Thr-Ala-Thr-Tyr-Gln-Phe (SEQ ID NO:22), or is an immunostimulatory homologue thereof from the corresponding region in another Yersinia species. Such homologues thus may contain substitutions, deletions or insertions of amino acid residues to accommodate strain to strain variation, provided that the homologues retain immunostimulatory properties. $(A)_n$ preferably includes a spacer, e.g., Gly—Gly, through which the Inv domain is linked to the peptide. In one preferred embodiment, $(A)_3$ is an invasin domain (Inv), glycine and glycine, in that order, i.e., (Inv)-Gly-Gly.

B is a spacer and is an amino acid which can be naturally occurring or the non-naturally occurring amino acids as described above. Each B is independently the same or different. The amino acids of B can also provide a spacer, e.g., Gly—Gly, between the promiscuous Th epitope and the FMDV VP1 antigenic site (e.g., SEQ ID NOS:1–21 and 35) or a reactive and immunologically functional analog thereof. In addition to physically separating the Th epitope from the B cell epitope, the Gly-Gly spacer can disrupt any artifactual secondary structures created by the joining of the Th epitope with the FMDV VP1 antigenic and thereby eliminate interference between the Th and/or B cell responses. The amino acids of B can also form a spacer which acts as a flexible hinge that enhances separation of the Th and FMDV VP1 target antigenic site. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro (SEQ ID NO:23), where Xaa is any amino acid, and preferably aspartic acid. The conformational separation provided by the amino acids of B permits more efficient interactions between the presented peptide immunogen and the appropriate Th cells and B cells and thus enhances the immune responses to the Th epitope and the antibody-eliciting epitope.

Th is a sequence of amino acids (natural or non-natural amino acids) that comprises a Th epitope. A Th epitope can consist of a continuous or discontinuous epitope. Hence not every amino acid of Th is necessarily part of the epitope. Accordingly, Th epitopes, including analogs and segments of Th epitopes, are capable of enhancing or stimulating an immune response to the FMDV VP1 antigenic site (e.g., SEQ ID NOS:1–21,35) and immunologically functional analogs thereof. Th epitopes that are immunodominant and promiscuous are highly and broadly reactive in animal and human populations with widely divergent MHC types (Partidos et al., 1991; U.S. Pat. No. 5,759,551). The Th domain of the subject peptides has from about 10 to about 50 amino acids and preferably from about 10 to about 30 amino acids. When multiple Th epitopes are present (i.e., $m \geq 2$), then each Th epitope is independently the same or different. Th segments are contiguous portions of a Th epitope that are sufficient to enhance or stimulate an immune response to the FMDV VP1 antigenic site.

Th epitopes of the present invention include as examples, but are not limited to, Th derived from foreign pathogens, for example HBs Th, HBc Th, PT Th, TT Th, MVF Th, CT Th, DT Th, DF Th, SM Th, and Tra Th; autologous Th from FMDV proteins (Table 5, e.g., SEQ ID NO:24), designed artificial Th (e.g., Table 6, SEQ ID NOS:25, 26, 36, 37, and 38), and immunologically functional analogs. Immunologically functional Th analogs include immune-enhancing analogs, reactive analogs and segments of any of these Th epitopes. Immunologically functional Th analogs preferably incorporate conservative substitutions, additions, deletions and insertions of from one to about 10 amino acid residues in the Th epitope which do not essentially modify the Th-stimulating function of the Th epitope.

"FMDV VP1 antigenic site" refers to amino acids 134–168 of the VP1 protein of FMDV $A_{12}$ strain (i.e., SEQ ID NO:1), and to peptides which are fragments of the VP1 protein of strains of FMDV other than the FMDV $A_{12}$ strain which are homologous to amino acids 134–139 of the VP1 protein of FMDV $A_{12}$ strain. FMDV VP1 antigenic site also refers to peptides having a consensus sequence derived from the amino acid sequence of the VP1 protein of FMDV strains of serotypes A, O or Asia, corresponding to amino acids 134–139 of the VP1 protein of FMDV $A_{12}$ strain; and peptides meeting the generic definitions of SEQ ID NOS: 14, 16, 18, and 20. FMDV VP1 antigenic site also refers to peptides which are members of an SSAL, as defined herein.

Reactive and immunologically functional analogs of the FMDV VP1 antigenic sites (e.g., SEQ ID Nos: 1–21, 35) according to the invention, may further comprise conservative substitutions, additions, deletions, or insertions of from one to about four amino acid residues provided that the peptide analogs are capable of eliciting immune responses reactive with the FMDV VP1 antigenic sites (e.g., SEQ ID NOS:1–21 and 35). The conservative substitutions, additions, and insertions can be accomplished with natural or non-natural amino acids as defined herein.

The target antigenic sites are preferably modified from that of the naturally occurring FMDV VP1 sequences of the G-H loop region by the substitutions for the native asparagine at position 134 and glutamine at position 157 by cysteines, and the formation of a disulfide bond between these cysteines so as to produce a cyclic structure (SEQ ID NO:2). These cyclic structures may also comprise 1 to 13 additional amino acids taken from either terminus of the 134–157 segment of VP1 provided that the single disulfide looped structure is preserved (SEQ ID NO:3). Modifications from native sequences are indicated by (N→C), (Q→C), (R→C) and by underlined amino acids, in Table 1. Peptide sequences containing introduced cysteines may be provided as SSALs, e.g. SEQ ID NOS: 15, 17, and 19, and these SSALs may be used as FMDV VP1 antigenic sites as well.

Accordingly, preferred peptide immunogens of this invention are the peptides containing the FMDV VP1 antigenic sites (e.g., SEQ ID NOS:1–21 and 35) or immunologically functional analogs thereof and Th peptides. The more preferred peptide immunogens are those constructs containing an FMDV VP1 antigenic site or a reactive and immunologically functional analog thereof; a spacer (e.g., Gly—Gly); a Th epitope that is an HBs Th, HBc Th, MVF Th, PT Th, TT Th, an autologous FMDV Th (e.g., SEQ ID NO:24) or an artificial Th (e.g., SEQ ID NOS:25, 26, 36, 37, and 38), or an analogue thereof; and, optionally, an Inv domain (SEQ ID NO:22) or analog thereof.

Vaccines which contain cocktails of the subject peptide immunogens with two or more of the Th epitopes may enhance immunoefficacy in a broader population and thus provide an improved immune response to the FMDV VP1 antigenic site.

The peptide immunogens of this invention can be made by chemical synthesis methods which are well known to the ordinarily skilled artisan. See, for example, Fields et al., Chapter 3 in *Synthetic Peptides: A User's Guide*, ed. Grant, W. H. Freeman & Co., New York, NY, 1992, p. 382. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431. Preparation of peptide constructs comprising structured synthetic antigen libraries (SSALs) for either B and T cell epitopes can be accomplished by providing a mixture of alternative amino acids for coupling at a given variable position, at the appropriate ratio as specified in the design.

After complete assembly of the desired peptide immunogen, the resin is treated according to standard procedures to cleave the peptide from the resin and deblock the functional groups on the amino acid side chains. The free peptide is purified by HPLC and characterized biochemically, for example, by amino acid analysis or by sequencing. Purification and characterization methods for peptides are well known to one of ordinary skill in the art.

Other chemical means to generate the synthetic peptide constructs of the invention containing VP1 G-H loops and Th sites include the ligation of the haloacetylated and the cysteinylated peptide through the formation of a "thioether" linkage. For example, a cysteine can be added to the C terminus of a Th-containing peptide and the thiol group of cysteine may be used to form a covalent bond to an electrophilic group such as an $N^{\alpha}$ chloroacetyl-modified or a maleimide-derivatized $\alpha$- or $\epsilon$-$NH_2$ group of a lysine residue attached to the N-terminus of a FMDV VP1 antigenic site (e.g., SEQ ID NOS: 1–21) or reactive and immunologically functional analogs thereof. In this manner, a construct with Th-(FMDV VP1 antigenic site) or its reverse, (FMDV VP1 antigenic site)-Th, may be obtained.

The subject immunogens may also be polymerized. Polymerization can be accomplished for example by reaction of the immunogen with a cross-linking agent, for example by reaction between glutaraldehyde and the —$NH_2$ groups of lysine residues, using routine methodology. By another method, a synthetic immunogen, such as for example "(A)$_n$-Th$_m$-Gly-Gly-(FMDV VP1 antigenic site)-X", can be polymerized or co-polymerized with another immunogen by utilization of an additional cysteine added to the N-terminus of the synthetic immunogen. The thiol group of the N-terminal cysteine can be used for the formation of a "thioether" bond with haloacetyl-modified amino acid or a maleimide-derivatized α-$NH_2$ or ε-$NH_2$ group of a lysine residue that is attached to the N-terminus of a branched polylysyl core molecule (e.g., $K_2K$, $K_4K_2K$ or $K_8K_4K_2K$). The subject immunogen may also be prepared as a branched polymer through synthesis of the desired peptide construct directly onto a branched poly-lysyl core resin (Wang et al., Science, 1991; 254: 285–288).

Alternatively, the longer synthetic peptide immunogens can be synthesized by well-known recombinant DNA techniques. Many standard manuals on molecular cloning technology provide detailed protocols to produce the peptides of the invention by expression of recombinant DNA and RNA. To construct a gene encoding a peptide of this invention, the amino acid sequence is reverse translated into a nucleic acid sequence, preferably using optimized codon usage for the organism in which the gene will be expressed. Next, a gene encoding the peptide is made, typically by synthesizing overlapping oligonucleotides which encode the peptide and necessary regulatory elements. The synthetic gene is assembled and inserted into the desired expression vector. The synthetic nucleic acid sequences encompassed by this invention include those which encode the peptides of the invention, immunologically functional homologs and analogs, and nucleic acid constructs characterized by changes in the non-coding sequences that do not alter the immunogenic properties of the peptide encoded thereby. Nucleic acids which comprise sequences that encode the peptides of this invention are also provided. The synthetic gene is inserted into a suitable cloning vecor and recombinants are obtained and characterized. The peptide is then expressed under conditions appropriate for the selected expression system and host. The peptide is purified and characterized by standard methods.

The efficacy of the peptide composition of the present invention can be established by injecting an animal, for example, guinea pigs and swine, with a formulation of immunogens (e.g., SEQ ID NOS:27–34,36) followed by monitoring the humoral immune response to the FMDV VP1 antigenic site (e.g., SEQ ID NOS:1–21,35, and reactive and immunologically functional homologues thereof), as exemplified in the Examples.

Another aspect of this invention provides a pharmaceutical composition comprising an immunologically effective amount of one or more of the peptide immunogens of this invention in a pharmaceutically acceptable delivery system. Accordingly, the subject peptides can be formulated as a vaccine composition using adjuvants, pharmaceutically-acceptable carriers or other ingredients routinely provided in vaccine compositions. Among the ingredients that can be used in this invention are adjuvants or emulsifiers including alum, incomplete Freund's adjuvant, liposyn, saponin, squalene, L121, emulsigen, monophosphoryl lipid A (MPL), QS21, ISA 35, ISA 206, and ISA 720 as well as the other efficacious adjuvants and emulsifiers. The formulations include formulations for immediate release and/or for sustained release, and for induction of systemic immunity and/or induction of localized mucosal immunity, which may be accomplished by, for example, immunogen entrapment by or coadministration with microparticles. Such formulations are readily determined by one of ordinary skill in the art. The present vaccines can be administered by any convenient route including subcutaneous, oral, intramuscular, or other parenteral or enteral route. Similarly the vaccines can be administered as a single dose or multiple doses. Immunization schedules are readily determined by the ordinarily skilled artisan.

The nucleic acids of this invention may themselves be useful as components of so-called "DNA vaccines". In this embodiment of the invention, expression of the immunogenic peptides of the invention is induced in the patient's own cells, by introduction into those cells of nucleic acids which encode the peptides. Methods of making and using DNA vaccines are disclosed in U.S. Pat. Nos. 5,580,859, 5,589,466, and 5,703,055; see also WO 97/02840 and W. McDonnell and F. Askari, New Engl. J. Med., 1996, 334:2–45, all of which are incorporated herein by reference. Such methods of making and using the peptides and peptide conjugates of this invention are contemplated to be within the scope of this invention.

The vaccine composition of the instant invention contain an effective amount of one or more of the peptide immunogens of the present invention and a pharmaceutically acceptable carrier. Such a composition in a suitable dosage unit form generally contains about 0.5 µg to about 1 mg of the immunogen per kg body weight. When delivered in multiple doses, it may be conveniently divided into an appropriate amount per dosage unit form. For example, an initial dose, e.g. 0.2–2.5 mg; preferably 1 mg, of immunogen represented as a peptide composition of the present invention, is to be administered by injection, preferably intramuscularly, followed by repeat (booster) doses. Dosage will depend on the age, weight and general health of the subject as is well known in the vaccine and therapeutic arts.

The immune response to FMDV VP1 antigenic site immunogens can be improved by delivery through entrapment in or on biodegradable microparticles of the type described by O'Hagan et al. (Vaccine, 1991; 9: 768–771). The immunogens can be encapsulated with or without an adjuvant in biodegradable microparticles, to potentiate immune responses, including localized mucosal immunity, and to provide time-controlled release for sustained or periodic responses, for oral administration, and for topical administration (O'Hagan et al, 1991; and, Eldridge et al., Molec Immunol, 1991; 28:287–294).

Such peptide compositions are useful to induce neutralizing antibodies to FMDV and as vaccines for the prevention and eradication of FMD.

Specific peptide immunogens and compositions are provided in the following examples to illustrate the invention. These examples are for purpose of illustration only, and are not to be construed as limiting the scope of the invention in any manner.

The target antigenic peptides of the Examples were synthesized by the solid-phase method outlined in Example 1. The FMDV VP1 antigenic site is exemplified by linear and cyclized peptides adapted from known viral isolates, including analogs and peptide homologues from other FMDV serotypes and subtypes (e.g., SEQ ID NOS:1–7) and consensus sites (e.g., SEQ ID NOS:8–13) and SSAL peptides (e.g., SEQ ID 14–21 and 35). Each peptide used for these examples has Gly—Gly spacers between immunogenic elements (e.g., SEQ ID NOS:30–32) but peptides of the invention may also have other spacers (e.g., SEQ ID NO:23) or no spacers. Th includes promiscuous helper sites derived from foreign pathogens such as hepatitis B virus and others incorporated herein by reference, autologous Th from FMDV (e.g., SEQ ID NO:24), and artificial Th (e.g., SEQ ID NOS:25, 26, and 36–38). Peptides of these examples also include an optional general immunostimulatory site (e.g., SEQ ID NO:22).

EXAMPLE 1

Typical Procedures for Evaluation of Target Antigenic Peptides

FMDV related synthetic peptides.

Peptides with sequence derived from the FMDV G-H loop domain of VP1 were synthesized by the Merrifield solid-phase synthesis technique on Applied Biosystems automated peptide synthesizers (Models 430, 431 and 433A) using Fmoc chemistry. Preparation of peptide constructs comprising structured synthetic antigen libraries (SSALs) for either B or T cell epitopes, e.g., "O SSAL" (SEQ ID NO:19) or "1,4,9 PALINDROMIC Th" (SEQ ID NO:26), was accomplished by providing a mixture of alternative amino acids for coupling at a given variable position, at the appropriate ratio as specified by subscripts in the design formulas for the SSALS as shown in FIGS. 2A, 3A, 3B, 4A, 4B or at an equimolar proportion if not specified in the design formula. After complete assembly of the desired peptide, the resin was treated according to standard procedure using trifluoroacetic acid to cleave the peptide from the resin and deblock the protecting groups on the amino acid side chains. For cyclic peptides, the cleaved peptide was dissolved in 15% DMSO in water for 48 hrs to facilitate intradisulfide bond formation between cysteines. The cleaved, extracted and washed peptides were purified by HPLC and characterized by mass spectrometry and reverse phase HPLC. They were to be used either as immunogens for vaccine development or as antigenic substrate for evaluation of their reactivity with sera obtained from immunized animals.

Guinea pig and swine immunizations.

Experimental groups of three Duncan Hartley guinea pigs (female, 9 weeks old, 450 gm, virus free), and swine (female, 9 weeks old) were used in immunogenicity studies of synthetic FMDV VP1 target antigenic peptide immunogens. Each animal was immunized intramuscularly with 100 µg per dose of a FMDV vaccine containing a peptide composition of the invention, either a single target antigenic peptide or a mixture thereof, emulsified in a specific adjuvant formulation at weeks 0 and 3. The animals were bled on weeks 0, 3, 5 and 8 or 10 for immunogenicity testing.

Immunogenicity evaluation.

Immunogenicity testing of the synthetic target antigenic peptide immunogens was by synthetic FMDV VP1 peptide-based ELISAs using corresponding FMDV VP1 target antigenic peptides containing only the target neutralizing site only as solid phase antigen. Serially diluted experimental animal sera were tested and positive titers were expressed as $Log_{10}$ of the reciprocal dilution. Seropositive samples were pooled by group and immunogenicity testing was extended by determinations of neutralization activity against various isolates of FMDV as described below.

Synthetic VP1 (AA134–169) peptide-based ELISAs.

Peptide-based ELISAs were conducted in peptide-coated 96-well plates coated by 1 hr incubation at 37° C. with FMDV VP1 site peptides at 5 µg/mL using 100 µL per well in 10 mL NaHCO$_3$ buffer, pH 9.5. The peptide coated wells were incubated with 250 µL of 3% by weight of gelatin in PBS at 37° C. for 1 hr to block non-specific protein binding sites, washed three times with PBS containing 0.05% by volume TWEEN 20 and then dried. Test samples were diluted with PBS containing 20% by volume normal goat serum, 1% by weight gelatin and 0.05% by volume TWEEN at dilutions of 1:20 volume to volume unless indicated otherwise. 100 µL of the diluted sample was added to each of the wells and allowed to react for 1 hr at 37° C. The wells were then washed six times with 0.05% by volume TWEEN 20 in PBS to remove unbound labeled antibodies. 100 PL of horseradish peroxidase labeled goat anti-guinea pig or anti-swine IgG at predetermined optimal dilution in 1% by volume normal goat serum, 0.05% by volume TWEEN 20 in PBS was added to each well and incubated at 37 C for 15 minutes. The wells were washed six times with 0.05% by volume TWEEN 20 PBS to remove unbound labeled antibody conjugate and reacted with 100 µL of the substrate mixture containing 0.04% by weight orthophenylenediamine (OPD) and 0.12% by volume hydrogen peroxide in sodium citrate buffer pH 5.0, for 15 minutes. Reactions were stopped by the addition of 100 µL of 1.0 M $H_2SO_4$ and the absorbance at 492 nm ($A_{492}$) was measured. ELISA titers, expressed as $Log_{10}$, were calculated based on linear regression analysis of the absorbances, with cutoff $A_{492}$ set at 0.5.

FMDV viruses.

The various strains of FMDV (e.g., $A_{12}$ and $A_{24}$ of serotype A; $O_1$, $O_2$, of serotype O, etc) were grown in monolayers of baby hamster kidney (BHK) cells, and purified, under containment at the Plum Island Animal Disease Center, USDA (Greenport, N.Y.) essentially as described by Brown and Cartwright (J Gen Microbiol, 1963; 31:179–186), with a treatment of the pellet by either 1% SDS or 1% Nonidet P-40 before centrifugation through a 15–45% sucrose gradient. Purified virus peaks were identified and isolated by pumping the contents of each centrifuge tube through the flow cell of a spectrophotometer set at 260 nm.

Serological evaluation of FMDV neutralization activity.

Serum samples were processed from blood collected from swine (cranial vena cava) and guinea pigs (cardiac puncture) and kept at −20° C. until tested. Enumeration of the viruses neutralized by a 1:100 dilution of serum samples was accomplished by neutralization determinations on a series of increasing input viral loads, using aliquots (10,000 MPD$_{50}$) of the various serotypes prepared as described above. By the testing method that was performed (Morgan and Moore, Am J Vet Res, 1990; 51:40–45), animals giving rise to sera which provide a 2.5 $Log_{10}$ reduction of FMDV microplaques at 1:100 dilution are highly predictive of protective immunity against FMDV infection.

EXAMPLE 2

Optimization of FMDV Target Antigenic Peptide by Sequence, Conformation and Immunostimulatory Elements Seven FMDV VP1 serotype A peptides are described in Table 7. Their corresponding VP1 amino acid sequences are aligned and numbered as in Table 1. The Th-bearing peptides of this group have the autologous FMDV Th identified as VP1 21–40 (SEQ ID NO:24) described in Table 5, of the following sequence: Glu-Thr-Gln-Ile-Gln-Arg-Arg-Gln-His-Thr-Asp-Val-Ser-Phe-Ile-Met-Asp-Arg-Phe-Val (SEQ ID NO:24). Inv is the invasin domain sequence (SEQ ID NO:22). The sequences for five of the seven constructs of Table 7 are detailed according to SEQ ID NOS: 1, 2, and 27–29. These peptides were synthesized and immune sera generated for immunogenicity evaluation. Sera obtained from five weeks post initial immunization were assayed for their FMDV VP1 peptide reactivity by peptide-ELISA and their ability to neutralize FMDV of serotype A by the standard FMDV neutralization assay using strain AFP as the target virus.

Potency of the sera was expressed as $Log_{10}$ anti-FMDV VP1 ELISA titer and $Log_{10}$ of FMDV $A_{FP}$ ($MPD_5$,) neutralized at a serum dilution of 1:100.

Results:

The $A_{12}$(134–159) peptides p2228a without Th and cyclization, and p2229c without cyclization elicited antipeptide antibody response in one out of three and two out of three of the animals respectively. In contrast, longer peptide p2224a, $A_{12}$ (134–169), and the longer cyclized peptides were immunogenic in three out of three animals. Also, cyclized $A_{12}$(134–159) peptide p2233c was immunogenic in three out of three guinea pigs. Among the immunoreactive serum samples, the ELISA titers were similar for all seven peptide constructs.

However, significant differences were observed between the peptide constructs as evaluated by serum neutralization activity (shown in Table 7) and graded as: p2228a<p2224a<p2229c<p2225c<p2223a<p2236c.

Based on this grading of neutralization efficacy, the following conclusions were drawn regarding optimization of FMDV VP1 antigenic peptide:

(1) Longer peptide constructs covering AA residues from 134–169 provide higher neutralization efficacy and are thus preferred than those of shorter sequences (AA134–159) (e.g., p2224a>p2228a, p2225c>p2229c, and p2236c>p2233c);

(2) Artificially cyclized synthetic constructs provide better conformation and are thus more preferred than their corresponding non-cyclized constructs (e.g., p2223a>p2229c and p2236c>p2225c);

(3) Synthetic constructs containing immunostimulatory elements provide higher neutralization efficacy and are thus more preferred than those without (e.g., p2236c>p2223a; p2229c>p2228a; and p2225c>p2224a).

EXAMPLE 3

Synthetic Constructs Employing Consensus Sequences for the Hypervariable Regions of VP1 Protein Provide for Broad FMDV Neutralization Two synthetic cyclic constructs employing consensus VP1 target antigenic sites were designed in accordance with a consensus serotype O sequence shown in Table 1 (SEQ ID NO: 11). One consensus peptide was synthesized with immunostimulatory elements including the Inv domain (SEQ ID NO:22) and the artificial SSAL Th shown in Table 6 (SEQ ID NO:26). The other was synthesized without additional immunostimulatory sequences. The overall structures of these FMDV VP1 constructs are depicted as p2569a in Table 8a (SEQ ID NO: 11) and p2570c in Table 8b (SEQ ID NO:30).

Sera obtained from hyperimmunized guinea pigs three and five weeks post initial immunization were evaluated for their FMDV VP1 peptide reactivities by peptide-ELISA and their ability to neutralize FMDV of multiple serotypes O, A and Asia by the standard FMDV neutralization assays using FMDV strains $A_{FP}$, O-1PI, O-1 Taiwan, $O_{Fran}$, $O_{Taiwan}$, $O_{Kauf}$ and Asia 1 as the target viruses.

High anti-FMDV VP1 peptide antibody titer was observed by week 3 after a single immunization demonstrating high immunopotency for both synthetic FMDV immunogens. However, the high neutralizing activity of the serum seen as early as 3 weeks post initial immunization, and the breadth of its specificity across serotypes A, O, and Asia, was unexpected. Neutralizing activity of such broad range is rarely observed for even the best FMDV vaccines prepared from inactivated virus stocks.

The consensus design for FMDV target antigenic peptide provides the basisl for an FMDV vaccine of broadly reactive neutralization activity.

EXAMPLE 4

Artificial Th and SSAL Target Antigenic Peptide for Improved FMDV VP1 Immunogenicity and Breadth of FMDV Neutralization Two target antigenic peptides, p1522b (SEQ ID NO:31) and p1592c (SEQ ID NO:32), were designed, each with a FMDV target antigenic site prepared as a structured synthetic antigen library (SSAL). These two peptides are described in Table 9. Th SSAL target antigenic site of p1522b (SEQ ID NO:31) is a complete representation of the G-H loop VP1 regions compiled from the subtypes of serotype O in Table 3. This target antigenic site was designed in accordance with the "O SSAL (COMPLETE)" sequence shown in FIG. 4B by SEQ ID NO:19. Similarly, p1592c comprises an SSAL target antigenic site that represents all the G-H loop sequences listed in Table 4 for subtypes of serotype Asia. This SSAL site for Asia was designed in accordance with the "Asia SSAL" sequence shown by SEQ ID NO:21. The artificial Th termed "Syn Th(1,2,4)" of Table 6 (SEQ ID NO:25) was linked to 1522b and p1592c for immunogenicity, and the Inv immunostimulatory site (SEQ ID NO:22) was coupled to p1592c.

These two SSAL target antigenic peptides were synthesized and used to hyperimmunize groups of 3 guinea pigs, as described (Example 1). Sera obtained from five and ten weeks post initial immunization were evaluated for their FMDV VP1 peptide reactivity by peptide-ELISA and their ability to neutralize FMDV of serotypes O, A and Asia by the standard FMDV neutralization assay using FMDV strains A1, $A12_{FP}$, $A_{FL}$, A23, O-$1_{JH}$, O-1 p2 and Asia 1 as the target viruses. Results are shown in Table 9.

High anti-peptide titers against the target antigenic sites (>5.0 $Log_{10}$) were evoked by both p1522b and p1592c by 5 weeks post initial immunization (earlier bleeds were not taken). Broad and effective FMDV neutralization of all seven FMDV strains belonging to three different serotypes (i.e., A, O and Asia) were observed for both anti-sera despite the wide variations in sequence between these strains and serotypes. This demonstrates the usefulness of SSAL in the design of a synthetic peptide based vaccine directed against a target antigenic/functional site of high variability.

The SSAL design for FMDV target antigenic peptides provide the basis for an FMDV vaccine of broadly reactive neutralization activity.

EXAMPLE 5

Multiple Serotype Mixture for Effective FMDV Neutralization

A mixture of three SSAL target antigenic peptides, having synthetic peptides p1520b, p1522b, and p1888b (SEQ ID NO:33,31, and 34) is described in Table 10. This mixture comprises SSAL target antigenic sites representing serotype A (SEQ ID NO:15, Table 2), serotype O (SEQ ID NO:19, Table 3), and serotype Asia (SEQ ID NO:35) linked to artificial Th epitope "Syn Th (1,2,4)" (SEQ ID NO:25). This mixture was used to immunize a group of 3 swine. Doses of 100 µg were administered 3 weeks apart in Freund's Complete Adjuvant on week 0 and Freund's Incomplete on week 3. Sera obtained after the initial immunization were evaluated for immunogenicity by peptide ELISA for the FMDV VP1 antigenic site and FMDV neutralization assay where a strain of unknown VP1 sequence, O1-Taiwan, from a recent outbreak, was employed as the target virus. All three pigs responded to the immunization with high anti-peptide reactivity (an average FMDV VP1 ELISA titer of 3.7 $Log_{10}$). Despite the unknown nature of the FMDV O1-Taiwan VP1 sequence, the 1:100 diluted and pooled serum obtained from the three immunized hosts demonstrated a significant neutralization activity of 4.5 $Log_0$. This level of neutralization activity is predictive of protective immunity for FMDV infection. Based on the extensive experience accumulated at the Plum Island Animal Disease Center, USDA (Morgan and Moore, 1990) for the prediction of a vaccine's FMDV protective nature, sera that can neutralize 2 $Log_{10}$ of FMDV ($MPD_{50}$) by in vitro assay predicted effective protection against FMDV infection in the vaccinated hosts.

This observation correlates immune response to vaccination by a peptide composition of the invention with protection from infection in swine, one of the vaccine's targeted hosts. It demonstrated the potential of an FMDV VP1 peptide composition of the invention to perform as an effective universal FMDV vaccine (i.e., effective against the antigenically variable isolates of multiple serotypes), an accomplishment not achieved since the introduction of inactivated FMDV vaccines in the early 1950s.

EXAMPLE 6

Peptides for Evaluation of Immunological Status

Peptides of the invention were incorporated into an ELISA test for evaluation of the serological reactivities of herds of known status regarding exposure to FMDV and vaccination. The peptides used were selected to be representative of the strains of FMDV used to vaccinate and were believed to be of the same serotype of the field strains to which the animals may have been exposed.

Kits for the diagnostic tests were prepared and used as described in the "Synthetic VP1 (AA134–169) peptide-based ELISAs" section of EXAMPLE 1. The plates were coated with VP1 peptides corresponding to strain $O1_{Campos}$ (p2463=AA128–158(T→C)-169) and strain $O1_{Manisa}$ (p2466=AA128–158(T→C)-169) as solid phase antigens. These kits were used to test serum samples collected from herds of a country which had experienced an outbreak of FMD 9 months previously. The herds were classified by their known status as "Infection Suspected" and "Infection Suspected with Vaccination" (from regions that experienced the outbreak), "Vaccinated", and "Normal" (from regions that were believed to be free of FMDV). Samples that displayed absorbances at or above a cutoff value of 0.2 times the absorbance for a Strong Reactive Control were scored as reactive. Results are shown in Table 11.

These results show that reactivity to the peptide-based ELISA is predictive of herd exposure. The herds that were exposed displayed significant reactivities of about 20% while animals from the normal herd had no reactivities. The 20% reactivity for the exposed herds may have been higher if the tests had been performed closer in time to the outbreaks than 9 months. The results for the vaccinated herds displayed a surprising amount of variability, reflective of high variability in the efficacy of various vaccination programs that used conventional vaccines obtained from several suppliers.

All of the references recited hereinabove are hereby incorporated by reference.

TABLE 1

| VP1 Sequence Alignment for Subtypes of FMDV from Serotypes A, O and Asia | | | | | | |
|---|---|---|---|---|---|---|
| | | 140 | 150 | 160 | 169 | |
| A12(134-169) | | NKYSASG | S-GVRGDFGS | LAPRVARQLP | ASFNYGAIK | (SEQ ID NO:1) |
| A12[134(N→C)-158(Q→C)-169]* | | CKYSASG | S-GVRGDFGS | LAPRVARCLP | ASFNYGAIK | (SEQ ID NO:2) |
| A12(125-134(N→C)-158(Q→C)-171) | VLATVY NGTCKYSASG | S-GVRGDFGS | LAPRVARCLP | ASFNYGAIKAE | | (SEQ ID NO:3) |
| O1 Caseros(134-169) | | CKYSSKA | VPNVRGDLNV | LEQKAARTLP | TSFNYGAIK | (SEQ ID NO:4) |
| O1 Caseros[134-158(T→C)-169] | | CKYSSKA | VPNVRGDLNV | LEQKAARCLP | TSFNYGAIK | (SEQ ID NO:5) |
| Asia 1(134-169) | | RPYGETT | S--RRGDMAA | LAQRLSARLP | TSFNYGAVK | (SEQ ID NO:6) |
| Asia 1[134-(R→C)-158(R→C)-169] | | CPYGETT | S--RRGDMAA | LAQRLSACLP | TSFNYGAVK | (SEQ ID NO:7) |
| CONSENSUS 'A'(134-169) | | NKYSVSG | S-GRRGDLGS | LAARVAKQLP | ASFNYGAIK | (SEQ ID NO:8) |
| CONSENSUS 'A'[134(N→C)-158(Q→C)-169] | | CKYSVSG | S-GRRGDLGS | LAARVAKCLP | ASFNYGAIK | (SEQ ID NO:9) |
| CONSENSUS "O"(134-169) | | CKYGENA | VTNVRGDLQV | LAQKAARTLP | TSFNYGAIK | (SEQ ID NO:10) |
| CONSENSUS "O"[134-158(T→C)-169] | | CKYGENA | VTNVRGDLQV | LAQKAARCLP | TSFNYGAIK | (SEQ ID NO:11) |
| CONSENSUS "Asia"(134-169) | | TTYGTQP | S--RRGDMAA | LAQRLSRRLP | TSFNYGAVK | (SEQ ID NO:12) |
| CONSENSUS "Asia"[134(T→C)-158(T→C)-169] | | CTYGTQP | S--RRGDMAA | LAQRLSRCLP | TSFNYGAVK | (SEQ ID NO:13) |

*(X→C): naturally occurring residue X is replaced by cysteine, shown underlined in sequence.

TABLE 2

VP1 Sequence Alignment for Subtypes of FMDV Serotype A

Group 1

```
                                                130        140         150         160         171
                                                 |          |           |           |           |
A12                                             VLATVY  NGTNKYSASG  S-GVRGDFGS  LAPRVARQLP  ASFNYGAIKAE   (# M10975)
SEQ ID NO:38

A22/Iraq/24/64                                  VLATVY  NGTSKYSAGG  T-GRRGDLGP  LAARVAAQLP  ASFNFGAIQAT   (#irq24-64)
SEQ ID NO:39

A22                                             VLATVY  NGTGKYSAGG  M-GRRGDLEP  LAARVAAQLP  ASFNFGAIQAT   (# M38362)
SEQ ID NO:40

A22 550 USSR/65                                 VLATVY  NGTSKYSAGG  M-GRRGDLEP  LAARVAAQLP  TSFNFGAIQAT   (# K03339)
SEQ ID NO:41

A24 Cruzeiro                                    VPATVY  NGTSKYAVGG  S-GRRGDMGS  LAARVAKQLP  ASFNYGAIKAT   (# M12905)
SEQ ID NO:42

A24 Cruzeiro Brazil/55                          VSATVY  NGTSKYAVGG  S-GRRGDMGS  LAARVVKQLP  ASFNYGAIKAD   (# K03340)
SEQ ID NO:43

A24 Cruzeiro California                         VPATVY  NGTSKYAVGG  S-GRRGDMGS  LAARVVKQLP  ASFNYGAIKAD   (# J02183)
SEQ ID NO:44

A32 Venezuela/70                                VLATVY  NGVSKYAVGG  S-GRRGDLGP  LAARVAKQLP  ASFNYGAIKAE   (# K03342)
SEQ ID NO:45

A81 Castellanos Arg/87 Population               VLATVY  NGTNKYTVSG  S-NRRGDLGS  LAARVAKALP  ASFNYGAIKAD   (#U62259)
AF1,2,5
SEQ ID NO:46

A81 Castellanos Arg/87 Population               VLATVY  NGTNKYTVSG  S-NRRGDLGS  LAARVAKALP  ASFNYGAIKAD   (# U62256)
AFc1
SEQ ID NO:47

A81 Castellanos Arg/87 clone A                  VLATVY  NGTNKYTVSG  S-NRRGDLGS  LAARVAKALP  ASFNYGAIKAD   (# U62255)
SEQ ID NO:48

A Venceslau                                     VLATVY  NGTSKYTVSG  S-GRRGDMGS  LAARVVKQLP  ASFNYGAIKAD   (# A06733)
SEQ ID NO:48

Aarg79 A/Argentina 79                           VLATVY  NGTSKYTVGG  S-GRRGDMGS  LAARVAKQLP  ASFNFGAVKAT   (# K03345)
SEQ ID NO:49

Aven76 A/Venceslau Brazil/76                    VLATVD  NGTSKYTVDG  S-GRRGDMGS  LAARVAKQLP  ASFNFGAIKAT   (# K03344)
SEQ ID NO:50
```

Group 2

```
A5 (Spain-86)                                   VLATVY  NGTNKYSTDG  P--RRGDMGS  LTARAAKQLP  ASFNYGAIRAD   (# M72587)
SEQ ID NO:51

A5 Parma (I) 1962                               VLATVY  NGTNKYSTGG  S--RRGDTGS  TTARAAKQLP  ASFNYGAIRAD   (# M16081)
SEQ ID NO:52

A5 France   1951                                VLATVY  NGTNKYSTDG  P--RRDDMGS  PAARAAKQLP  ASFNYGAIRAD   (# M16079)
SEQ ID NO:53

A5 Westerwald/58                                VLATVY  NGTNKYSTGG  P--RRGDTWA  PAARAAKQLP  ASFNYGAIRAD   (# K03343)
SEQ ID NO:54

A10 (A-Holland)                                 VLATVY  NGTSKYSASG  S--RRGDLGS  LATRVATQLP  ASFNYGAIKAQ   (# M20715)
SEQ ID NO:55

A10-61                                          VLATVY  DGTNKYSASD  S--RSGDLGS  IAARVATQLP  ASFNYGAIQAQ   (# X00429)
SEQ ID NO:56

A22 Tamil Nadu India                            VLATVY  TGTSKYPSAG  R--RRGDLGP  LRQEDRRQLP  ASFNFGAVRAT   (# X88860)
SEQ ID NO:57

A22 Cuddapah, A.P.India                         VLANVY  NRTGRSSPDR  T--RRGDLGP  PLARYRRQPS  CSFNFGAVRAT   (# X88859)
SEQ ID NO:58

A22 India                                       VLATVY  NGTSKYSAPG  R--RRGDLGP  LLGEDRRQLP  ASFNFGAVRAT   (# X88858)
SEQ ID NO:59
```

TABLE 2-continued

| VP1 Sequence Alignment for Subtypes of FMDV Serotype A | | | |
|---|---|---|---|
| A27 Cundina-Marca Colombia/76<br>SEQ ID NO:60 | VLATVY NFTNKYSNGG Q--RAGDMGS LAARVAKQLP ASFNYGAIKAQ | (# K03341) |
| A Ostdeutchland (DDR) 1947<br>SEQ ID NO:61 | LATVY NGTSKYSASG L--GPGDLGS PAARVATQLP ASFNYGAIRAQ | (# M16093) |
| A Portugal (P) 1983<br>SEQ ID NO:62 | VLATVY NGTNKYSTDG P--RRGDMGS LTARAAKQLP XXXNYGAIRAV | (# M16092) |
| A Morocco (MA) 1983<br>SEQ ID NO:63 | VLATVY NGTNKYSTDG P--RRDDMGS PAARAAKQLP ASFNYGAIRAV | (# M16090) |
| A Madrid (E) 1983<br>SEQ ID NO:64 | VLATVY NGTNKYSTDG P--RRGDMGS LTARAAKQLP ASFNYGAIRAD | (# M16084) |
| A Modena (I) 1984<br>SEQ ID NO:65 | VLATVY NGTNKYSTGG S--RRGDTGS TAARAAKQLP ASFNYGAIRAD | (# M16082) |
| A/SAU/12/86<br>SEQ ID NO:66 | NGTSKSPRLG V--YGGPRPR TIGKTCAQLP ASFNFGAIKAT | (# M38458) |

TABLE 3

| VP1 Sequence Alignment for Subtypes of FMDV Serotype O | | |
|---|---|---|
| |    130      140      150      160      171 | |
| O1 Caseros | VLATVY NGECKYSSKA VPNVRGDLNV LEQKAARTLP TSFNYGAIKAT | (# U82271) SEQ ID NO:67 |
| O1 Caseros | VLATVY NGECKYSSXA VPNVRGDLNV LEQKAARTLP TSFNYGAIKAS | (# M89900) SEQ ID NO:68 |
| O1 Caseros India Arg/82 | VLATVY NGECKYSSNA VPNVRGDPNV LEQKAARTLP XXXXXXXXXT | (# Z21861) SEQ ID NO:69 |
| O-2-Brescia | VLATVY NGESRYSRNA VPNVRGDLQA LAQKAARTLP TSFNYGAIRAT | (# M55287) SEQ ID NO:70 |
| O OEK | VLATVY NGNCQYGKSS VTNVRGDLQV LAQKAARALP TSFNYGAIKAT | (# X88862) SEQ ID NO:71 |
| O/R2/75 | VLATVY NGNCKYGDGA VTNIRGDLQV LAQKAARALP TSFNYGAIKAT | (# X88863) SEQ ID NO:72 |
| O1 | VLATVY NGECRYNRNA VPNLRGDLQV LAQKVARTLP TSFNYGAIKAT | (# X00871) SEQ ID NO:73 |
| O Snir | VLATVY NGECRYGESS VTAVRGDLQV LARKAARTLP TSFNYGAIKAT | (# S77355) SEQ ID NO:74 |
| O1SL South Lebanon | VLATVY NGNCRYGESS VTAVRGDLQV LARKAARTLP TSFNYGAIKAT | (# S77354) SEQ ID NO:75 |
| O Karnataka India | VLASCY NGNCKYGDGT VTNIRGDQQV LAQKAARALP TSFNYGAIKAT | (# X88861) SEQ ID NO:76 |
| O Tunisia mateur/89 | VLATVY NGNCKYGSSH VANVRGDLQV LSQKAERTLP TSFNYGAIKAT | (# Z21859) SEQ ID NO:77 |
| O Golan Isr/81 | VLATVY NGNCRYGNVA VTNVRGDLQV LAQKAARTLP TSFNYGAIKXT | (# Z21860) SEQ ID NO:78 |
| O Yrigoyen Arg/82 | VLATVY NGECTYSSNA VPNVRGDPNL LEQKAARMLP AYFNYGAIKAT | (# Z21862) SEQ ID NO:79 |
| O-1-BFS | VLATVY NGECRYSRNA VPNLRGDLQV LAQKVARTLP TSFNYGAIKAT | (# J02185) SEQ ID NO:80 |
| O (isolate OBEK) | VLATVY NGNCKYGENS VTNIRGDLQV LAQKAARALP TSFNYGAIKAT | (# X99066) SEQ ID NO:81 |
| O (isolate OBAN) | VLATVY NGNCKYGTNA VTNIRGDLQV LAQKAARALP TSFNYGAIKAT | (# X99070) SEQ ID NO:82 |
| O (isolate ONDRI) | VLATVY NGNCKYGESS VTNVRGDLQV LAQKAARTLP TSFNYGAIKAT | (# X99069) SEQ ID NO:83 |
| O (isolate 310) | VLATVY QRNCKYGDGA VTNIRGDLQV LAQKAARALP TSFNYGAIKAT | (# X99068) SEQ ID NO:84 |
| O (isolate 157) | VLASVY YGYCKYGDGG VTNIRGDLQV LAQKAARALP TSFNYGAIKAT | (# X99065) SEQ ID NO:85 |
| O (isolate 56) | VLATVY NRNCKYGEWS VTNIRGDLQV LAQKAARALP TSFNYGAIKAT | (# X99067) SEQ ID NO:86 |

TABLE 4

VP1 Sequence Alignment for Subtypes of FMDV Serotype Asia

```
                                                      130            141     150         160          171
                                                       |              |       |           |            |
Asia 1 Nainital, U.P. (vaccine strain) (# X88855)   VLATVY   NGKTTYGTQP T--RRGDLAV LAQRVSNRLP TSFNYGAVKAD
SEQ ID NO:87

Asia 1 Mandya,Karnataka   (# X88856)                VLATVY   NGKPTYGKQP S--RRGDMAA LAQRLSRQLP TSFNYGAVKAE
SEQ ID NO:88

Asia 1 Nilgiri, Tamil Nadu  (# X88857)              VLATVY   NGKTTYGEQP S--RRGDMAA LAQRLSRQLP TSFNYGAVKAE
SEQ ID NO:89

Asia 1 STRAIN 63/72 (# Y09949)                      VLATVY   NGKTTYGTQP T--RRGDLAV LAQRVSNRLP TSFNYGAVKAD
SEQ ID NO:90

Asia 1 (# U01207)                                   VLATVY   NGKRPYGETT S--RRGDMAA LAQRLSARLP TSFNYGAVKAD
SEQ ID NO:91
```

TABLE 5

FMDV T Cell Helper Epitopes (Th)

| Source of FMDV Th | Host Species | Reference |
|---|---|---|
| VP1 (35–53) | Cattle | Van Lierop et al., Immunology 84:79, 1995 |
| VP2 (74–88) | Cattle | Van Lierop et al., Immunology 84:79, 1995 |
| VP4 (20–34) | Cattle | Collen et al., J. (Gen. Virology 71:309, 1990 |
| VP1 (21–40) (SEQ ID NO:24) | Cattle | Collen et al., J. Immunology 146:749, 1991 |
| VP1 (135–144) | Mouse | Zarorano et al., Virology 212:614, 1995 |
| VP1 (62–76) | Pig | Rodriguez et al., Virology 205:24, 1994 |
| VPl (83–104) | Pig | Rodriguez et al., Virology 205:24, 1994 |
| VP1 (188–209) | Pig | Rodriguez et al., Virology 205:24; 1994 |
| VP1 (111–132) | Pig | Rodriguez et al., Virology 205:24, 1994 |

TABLE 6

Sequences for Artificial T Cell Helper Epitopes (Th)

| Description | Amino acid Sequence | Seq. ID No. |
|---|---|---|
| Syn Th(1, 2, 4) | KKKIITTRIITIITTID | SEQ ID NO: 25 |
| IS(1, 4, 9 PALINDROMIC)LF simplified Th | ISISEIKGVIVHKIEGILF<br>T   RT    TR   T | SEQ ID NO: 26 |
| IS(1, 4, 9 PALINDROMIC)LF Th | ISISEIKGVIVHKIEGILF<br>MT   RT    TRM   TM<br>L           L   V | SEQ ID NO: 38 |
| (1, 4, 9 PALINDROMIC)Th | ISEIKGVIVHKIEGI<br>MT   RT    TRM   TM<br>L           L   V | SEQ ID NO: 36 |
| (1, 4, 9 PALINDROMIC) simplified Th | ISEIKGVIVHKIEGI<br>T   RT    TR   T | SEQ ID NO: 37 |

TABLE 7

Optimization of FMDV Target Antigenic Peptide by Sequence, Conformation and Immunostimulatory Elements

| Peptide Code | Description of Target Antigenic Peptide | Seq. ID No. | No. of Animals Responding[c] (n = 3) | LOG$_{10}$ Anti-FMDV-VP1 ELISA Titer[d] | Log$_{10}$ of FMDV-A$_{FP}$ (MPD50) neutralized by serum[d,e] |
|---|---|---|---|---|---|
| p2228a | A$_{12}$(134–159) | | 1 | 4.144 | 2.5 |
| p2229c | Inv-GG-VP1$_{(21-40)}$Th-GG-A$_{12}$(134–159) | | 2 | 4.188 | 5.5 |
| p2233c | Inv-GG-VP1$_{(21-40)}$Th-GG-A$_{12}$[134 (N→C)[a]-158(Q→C)[b]-159] | SEQ ID NO: 27 | 3 | 3.987 | 7.0 |
| p2224a | A$_{12}$(134–169) | SEQ ID NO: 1 | 3 | 3.395 | 4.5 |
| p2225c | Inv-GG-VP1$_{(21-40)}$Th-GG-A$_{12}$(134–169) | SEQ ID NO: 28 | 3 | 5.120 | 6.0 |
| p2223a | A$_{12}$[134(N→C)[a]-158(Q→C)[b]-169] | SEQ ID NO: 2 | 3 | 5.489 | 7.0 |
| p2236c | Inv-GG-VP1$_{(21-40)}$TH-GG-A$_{12}$[134 (N→C)[a]-158(Q→C)[b]-169] | SEQ ID NO: 29 | 3 | 4.333 | 8.0 |

[a]N$_{134}$ of the native VP1 sequence is replaced by C.
[b]Q$_{158}$ of the native VP1 sequence is replaced by C.
[c]No. of animals responding from groups of 3 at 5 weeks post initial immunization.
[d]Test results for pooled sera from ELISA-reactive animals.
[e]Serum for neutralization assays diluted 1:100.

TABLE 8

Consensus Target Antigenic Peptide for Broad FMDV Neutralization

| Peptide code | Description of Target Antigenic Peptide | Seq. ID No. | WPI[b] | No. of Animals Responding (n = 3) | Log$_{10}$ Anti-FMDV-VP1 ELISA Titer[c] | Log$_{10}$ of FMDV (MPD$_{50}$) Neutralized by Serum[c,d] | | | | |
|---|---|---|---|---|---|---|---|---|---|---|
| | | | | | | O$_{Fran}$ | O$_{Taiwan}$ | O$_{Kauf}$ | A$_{FP}$ | Asia 1 |
| p2569a | O Consensus[134–158 (T→C)$^a$-169] | SEQ ID NO: 11 | 5 | 3 | 4.1 | 3.0 | 3.5 | 2.0 | 2.5 | 3.5 |

SSAL Th and Consensus Target Antigenic Peptide for Broad FMDV Neutralization

| Peptide code | Description of Target Antigenic Peptide | Seq. ID No. | WPI[b] | No. of Animals Responding (n = 3) | Log$_{10}$ Anti-FMDV-VP1 ELISA Titer[c] | Log$_{10}$ of FMDV (MPD$_{50}$) Neutralized by Serum[c,d] | | | |
|---|---|---|---|---|---|---|---|---|---|
| | | | | | | A$_{12}$ FP | O-1 PI | O-1 Taiwan | Asia 1 |
| p2570c | Inv-GG-IS (1, 4, 9 PALINDROMIC)LF simplified Th-GG-O $_{Consensus}$[129–158(T→C)$^a$-169] | SEQ ID NO: 30 | 3 5 | 2/3 2/3 | 4.155 4.864 | 2.5 2.5 | 4.0 | 4.5 5.0 | 1.5 2.0 |

$^a$T$_{158}$ of the native sequence was replaced by C.
$^b$Weeks post initial immunization.
$^c$Reactivities for pooled sera from ELISA-reactive animals.
$^d$Serum for neutralization assays diluted 1:100.

TABLE 9

Artificial Th and SSAL Target Antigenic Peptides for Improved Immunogenicity and Breadth of FMDV Neutralization

| Peptide Code | Target Antigenic Peptide | SEQ ID NO: | WPI | No. of Animals Responding (n = 3) | Log$_{10}$ Anti-FMDV-VP1[d] ELISA Titer | Log$_{10}$ of FMDV (MPD$_{50}$) Neutralized by Serum[d,e] | | | | | | |
|---|---|---|---|---|---|---|---|---|---|---|---|---|
| | | | | | | A$_{12}$ FP | O-1 (JH) | A$_{FL}$ | O-1 P2 | A-23 | Asia 1 | A 1 |
| p1522b | Syn Th (1, 2, 4)-GG-O$_{Complete\ SSAL}$[134–158 (T→C)$^a$-169], cyclized | SEQ ID NO: 31 | 5 10 | 3 | 5.158 | 3.0 | ≥4.5 | 2.0 | 2.5 | 4.5 | ≥6.0 | 5.0 |
| p1592c | Inv-GG-Syn Th (1, 2, 4) 1-GG-Asia $_{SSAL}$[134(T→C)$^b$-158(R→C)$^c$-169], cyclized | SEQ ID NO: 32 | 5 10 | 3 | 5.256 | 3.0 | ≥4.5 | 2.0 | 1.0 | 3.0 | 2.5 | 4.5 |

$^a$T$_{158}$ of the native sequence was replaced by C.
$^b$T$_{134}$ of native sequence was replaced by C.
$^c$R$_{158}$ of the native sequence was replaced by C.
$^d$Reactivities of pooled sera from ELISA-reactive animals.
$^e$Serum for neutralization assays diluted 1:100.

TABLE 10

Multi-Serotype Mixture for Effective FMDV Neutralization

| Peptide Code | Description of FMDV VP1 Vaccine Constructs | Seq. ID No. | No. of Animals Responding (n = 3) | Log$_{10}$ Anti-FMDV-VP1 ELISA Titer[b] | Log$_{10}$ of FMDV O1- Taiwan neutralized by serum[b,c] |
|---|---|---|---|---|---|
| p1520b+ | Syn Th(1,2,4)-GG-A(1)$_{Complete\ ssAL}$(134(N→C-158(Q→C)-169),+ | SEQ ID NO: 33 | 3[a] | 3.688 | 4.5 |
| p1522b+ | Syn Th(1,2,4)-GG-O$_{Complete\ ssAL}$[134-158(T→C)-169],+ | SEQ ID NO: 31 | | | |
| p1888b | Syn Th(1,2,4)-GG-[d]A2/Asia$_{adjusted\ ssAL}$[134(N→C)-158(Q→C)-169] | SEQ ID NO: 34 | | | |

[a]Serum samples were collected at 3 weeks post-initial immunization.
[b]Test results for pooled sera from the ELISA-reactive animals.
[c]Serum for neutralization assays diluted 1:100.
[d]A2/Asia$_{adjusted\ ssAL}$[134(N→C)-158(Q→C)-169](SEQ ID NO.: 35)

TABLE 11

Reactivity By ELISA for Herds of Known Immunological Status

| Species | Herd Status | n | No. ELISA Reactive | % ELISA Reactive |
|---|---|---|---|---|
| swine | Infection suspected | 108 | 21 | 19.4% |
| swine | Infection suspected with vaccination | 70 | 16 | 22.8% |
| swine | Vaccinated | 100 | 92 | 92.0% |
| swine | Vaccinated | 31 | 17 | 54.8% |
| swine | Vaccinated | 70 | 26 | 37.1% |
| goat | Vaccinated | 288 | 155 | 53.8% |
| bovine | Vaccinated | 33 | 5 | 15.1% |
| bovine | Vaccinated | 30 | 2 | 6.7% |
| swine | Normal | 100 | 0 | 0% |

We claim:

1. A peptide selected from the group consisting of
    (i) SEQ ID NO:1;
    (ii) peptides, which are fragments of the VP1 protein of strains of FMDV other than the FMDV $A_{12}$ strain, and which are homologous to amino acids 134–168 of the VP1 protein of FMDV $A_{12}$ strain;
    (iii) peptides consisting of a consensus sequence derived from the amino acid sequence of the VP1 protein of FMDV strains of serotypes A, O or Asia, corresponding to amino acids 134–168 of the VP1 protein of FMDV $A_{12}$ strain;
    (iv) peptides meeting the definitions of SEQ ID NOS: 14, 16, 18, and 20;
    (v) peptides as defined in (i) through (iv) above, wherein the amino acids present at positions corresponding to amino acids 134 and 157 of the VP1 protein of FMDV $A_{12}$ strain have been replaced by cysteines; and
    (vi) peptides as defined in (i) through (v) above further consisting of 1 to 13 additional amino acids taken from either terminus of the 134–157 segment of VP1.

2. A peptide having an amino acid sequence which comprises:
    (i) the amino acid sequence of a peptide of claim 1, and
    (ii) the amino acid sequence of a helper T cell epitope (Th).

3. A peptide having an amino acid sequence which comprises:
    (i) the amino acid sequence of a peptide of claim 2, and
    (ii) the amino acid sequence of a general immunostimulatory sequence.

4. The peptide of claim 1 wherein the amino acids present at positions corresponding to amino acids 134 and 157 of the VP1 protein of FMDV $A_{12}$ strain have been replaced by cysteines.

5. The peptide of claim 4 wherein at least one peptide is selected from the group consisting of SEQ ID NO:2 and homologous sequences derived from other strains of FMDV.

6. The peptide of claim 1 in which the peptide is a peptide defined in (v).

7. The peptide of claim 6 wherein at least one peptide is selected from the group consisting of SEQ ID NO:3 and homologous sequences derived from other strains of FMDV.

8. The peptide of claim 1 selected from the group consisting of SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

9. A structured synthetic antigen library wherein said library comprises a plurality of peptides selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:35.

10. A method of diagnosing FMDV infection in a mammal, comprising the steps of:
    (a) attaching a peptide according to claim 1 to a solid support,
    (b) exposing said peptide attached to said solid support to a sample containing antibodies from said mammal, under conditions conducive to binding of the antibody to the peptide, and
    (c) detecting the presence of antibodies bound to said peptide attached to said solid support.

* * * * *

SEQUENCE LISTING (1) GENERAL INFORMATION:

(iii) NUMBER OF SEQUENCES: 91

(2) INFORMATION FOR SEQ ID NO:1:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:1:

Asn Lys Tyr Ser Ala Ser Gly Ser Gly Val Arg Gly
1               5                   10

Asp Phe Gly Ser Leu Ala Pro Arg Val Ala Arg Gln
            15                  20

Leu Pro Ala Ser Phe Asn Tyr Gly Ala Ile Lys
25                  30                  35

(2) INFORMATION FOR SEQ ID NO:2:

(i) SEQUENCE CHARACTERISTICS:

(A) LENGTH: 35 amino acids
            (B) TYPE: amino acid
            (D) TOPOLOGY: linear (ii) MOLECULE TYPE: peptide (xi) SEQUENCE DESCRIPTION: SEQ ID NO:2:

Cys Lys Tyr Ser Ala Ser Gly Ser Gly Val Arg Gly
1               5                   10

Asp Phe Gly Ser Leu Ala Pro Arg Val Ala Arg Cys
            15                  20

Leu Pro Ala Ser Phe Asn Tyr Gly Ala Ile Lys
25                  30                  35

(2) INFORMATION FOR SEQ ID NO:3:

(i) SEQUENCE CHARACTERISTICS:
            (A) LENGTH: 46 amino acids
            (B) TYPE: amino acid
            (D) TOPOLOGY: linear (ii) MOLECULE TYPE: peptide (xi) SEQUENCE DESCRIPTION: SEQ ID NO:3:

Val Leu Ala Thr Val Tyr Asn Gly Thr Cys Lys Tyr
1               5                   10

Ser Ala Ser Gly Ser Gly Val Arg Gly Asp Phe Gly
            15                  20

Ser Leu Ala Pro Arg Val Ala Arg Cys Leu Pro Ala
25                  30                  35

Ser Phe Asn Tyr Gly Ala Ile Lys Ala Glu
            40                  45

(2) INFORMATION FOR SEQ ID NO:4:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (xi) SEQUENCE DESCRIPTION: SEQ ID NO:4:

Cys Lys Tyr Ser Ser Lys Ala Val Pro Asn Val Arg
1               5                   10

Gly Asp Leu Asn Val Leu Glu Gln Lys Ala Ala Arg
            15                  20

Thr Leu Pro Thr Ser Phe Asn Tyr Gly Ala Ile Lys
25                  30                  35

(2) INFORMATION FOR SEQ ID NO:5:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (xi) SEQUENCE DESCRIPTION: SEQ ID NO:5:

Cys Lys Tyr Ser Ser Lys Ala Val Pro Asn Val Arg
1               5                   10

Gly Asp Leu Asn Val Leu Glu Gln Lys Ala Ala Arg
            15                  20

```
Cys Leu Pro Thr Ser Phe Asn Tyr Gly Ala Ile Lys
 25                  30                  35

(2) INFORMATION FOR SEQ ID NO:6:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:6:

Arg Pro Tyr Gly Glu Thr Thr Ser Arg Arg Gly Asp
 1               5                  10

Met Ala Ala Leu Ala Gln Arg Leu Ser Ala Arg Leu
            15                  20

Pro Thr Ser Phe Asn Tyr Gly Ala Val Lys
 25                  30

(2) INFORMATION FOR SEQ ID NO:7:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:7:

Cys Pro Tyr Gly Glu Thr Thr Ser Arg Arg Gly Asp
 1               5                  10

Met Ala Ala Leu Ala Gln Arg Leu Ser Ala Cys Leu
            15                  20

Pro Thr Ser Phe Asn Tyr Gly Ala Val Lys
 25                  30

(2) INFORMATION FOR SEQ ID NO:8:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:8:

Asn Lys Tyr Ser Val Ser Gly Ser Gly Arg Arg Gly
 1               5                  10

Asp Leu Gly Ser Leu Ala Ala Arg Val Ala Lys Gln
            15                  20

Leu Pro Ala Ser Phe Asn Tyr Gly Ala Ile Lys
 25                  30                  35

(2) INFORMATION FOR SEQ ID NO:9:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:9:
```

```
Cys Lys Tyr Ser Val Ser Gly Ser Gly Arg Gly
1               5                   10

Asp Leu Gly Ser Leu Ala Ala Arg Val Ala Lys Cys
            15              20

Leu Pro Ala Ser Phe Asn Tyr Gly Ala Ile Lys
25                  30                  35
```

(2) INFORMATION FOR SEQ ID NO:10:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:10:

```
Cys Lys Tyr Gly Glu Asn Ala Val Thr Asn Val Arg
1               5                   10

Gly Asp Leu Gln Val Leu Ala Gln Lys Ala Ala Arg
            15              20

Thr Leu Pro Thr Ser Phe Asn Tyr Gly Ala Ile Lys
25                  30                  35
```

(2) INFORMATION FOR SEQ ID NO:11:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:11:

```
Cys Lys Tyr Gly Glu Asn Ala Val Thr Asn Val Arg
1               5                   10

Gly Asp Leu Gln Val Leu Ala Gln Lys Ala Ala Arg
            15              20

Cys Leu Pro Thr Ser Phe Asn Tyr Gly Ala Ile Lys
25                  30                  35
```

(2) INFORMATION FOR SEQ ID NO:12:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:12:

```
Thr Thr Tyr Gly Thr Gln Pro Ser Arg Arg Gly Asp
1               5                   10

Met Ala Ala Leu Ala Gln Arg Leu Ser Arg Arg Leu
            15              20

Pro Thr Ser Phe Asn Tyr Gly Ala Val Lys
25                  30
```

(2) INFORMATION FOR SEQ ID NO:13:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:13:

Cys Thr Tyr Gly Thr Gln Pro Ser Arg Arg Gly Asp
1               5                   10

Met Ala Ala Leu Ala Gln Arg Leu Ser Arg Cys Leu
            15                  20

Pro Thr Ser Phe Asn Tyr Gly Ala Val Lys
25              30

(2) INFORMATION FOR SEQ ID NO:14:

(i) SEQUENCE CHARACTERISTICS:
         (A) LENGTH: 35 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Asn, Ser or Gly"

(ix) FEATURE:
         (A) NAME/KEY: Modified-site
         (B) LOCATION: 4
         (D) OTHER INFORMATION: /note= "Ser, Thr or Ala"

(ix) FEATURE:
         (A) NAME/KEY: Modified-site
         (B) LOCATION: 5
         (D) OTHER INFORMATION: /note= "Val or Ala"

(ix) FEATURE:
         (A) NAME/KEY: Modified-site
         (B) LOCATION: 6
         (D) OTHER INFORMATION: /note= "Ser, Gly or Asp"

(ix) FEATURE:
         (A) NAME/KEY: Modified-site
         (B) LOCATION: 8
         (D) OTHER INFORMATION: /note= "Ser, Thr or Met"

(ix) FEATURE:
         (A) NAME/KEY: Modified-site
         (B) LOCATION: 9
         (D) OTHER INFORMATION: /note= "Gly or Asn"

(ix) FEATURE:
         (A) NAME/KEY: Modified-site
         (B) LOCATION: 10
         (D) OTHER INFORMATION: /note= "Arg or Val"

(ix) FEATURE:
         (A) NAME/KEY: Modified-site
         (B) LOCATION: 14
         (D) OTHER INFORMATION: /note= "Leu, Met or Phe"

(ix) FEATURE:
         (A) NAME/KEY: Modified-site
         (B) LOCATION: 15
         (D) OTHER INFORMATION: /note= "Gly or Glu"

(ix) FEATURE:
         (A) NAME/KEY: Modified-site
         (B) LOCATION: 16
         (D) OTHER INFORMATION: /note= "Ser or Pro"

(ix) FEATURE:
         (A) NAME/KEY: Modified-site
         (B) LOCATION: 19
         (D) OTHER INFORMATION: /note= "Ala or Pro"

```
        (ix) FEATURE:
              (A) NAME/KEY: Modified-site
              (B) LOCATION: 22
              (D) OTHER INFORMATION: /note= "Ala or Val"

(ix) FEATURE:
              (A) NAME/KEY: Modified-site
              (B) LOCATION: 23
              (D) OTHER INFORMATION: /note= "Lys, Arg or Ala"

(ix) FEATURE:
              (A) NAME/KEY: Modified-site
              (B) LOCATION: 24
              (D) OTHER INFORMATION: /note= "Gln or Ala"

(ix) FEATURE:
              (A) NAME/KEY: Modified-site
              (B) LOCATION: 27
              (D) OTHER INFORMATION: /note= "Ala or Thr"

(ix) FEATURE:
              (A) NAME/KEY: Modified-site
              (B) LOCATION: 31
              (D) OTHER INFORMATION: /note= "Tyr or Phe"

(ix) FEATURE:
              (A) NAME/KEY: Modified-site
              (B) LOCATION: 34
              (D) OTHER INFORMATION: /note= "Ile or Val"

(ix) FEATURE:
              (A) NAME/KEY: Modified-site
              (B) LOCATION: 35
              (D) OTHER INFORMATION: /note= "Lys or Gln"

(xi) SEQUENCE DESCRIPTION: SEQ ID NO:14:

Xaa Lys Tyr Xaa Xaa Xaa Gly Xaa Xaa Xaa Arg Gly
1               5                   10

Asp Xaa Xaa Xaa Leu Ala Xaa Arg Val Xaa Xaa Xaa
        15                  20

Leu Pro Xaa Ser Phe Asn Xaa Gly Ala Xaa Xaa
25                  30                  35

(2) INFORMATION FOR SEQ ID NO:15:

(i) SEQUENCE CHARACTERISTICS:
              (A) LENGTH: 35 amino acids
              (B) TYPE: amino acid
              (D) TOPOLOGY: linear (ii) MOLECULE TYPE: peptide (ix) FEATURE:
              (A) NAME/KEY: Modified-site
              (B) LOCATION: 4
              (D) OTHER INFORMATION: /note= "Ser, Thr or Ala"

(ix) FEATURE:
              (A) NAME/KEY: Modified-site
              (B) LOCATION: 5
              (D) OTHER INFORMATION: /note= "Val or Ala"

(ix) FEATURE:
              (A) NAME/KEY: Modified-site
              (B) LOCATION: 6
              (D) OTHER INFORMATION: /note= "Ser, Gly or Asp"

(ix) FEATURE:
              (A) NAME/KEY: Modified-site
              (B) LOCATION: 8
              (D) OTHER INFORMATION: /note= "Ser, Thr or Met"

(ix) FEATURE:
              (A) NAME/KEY: Modified-site
              (B) LOCATION: 9
```

```
            (D) OTHER INFORMATION: /note= "Gly or Asn"

(ix) FEATURE:
            (A) NAME/KEY: Modified-site
            (B) LOCATION: 10
            (D) OTHER INFORMATION: /note= "Arg or Val"

(ix) FEATURE:
            (A) NAME/KEY: Modified-site
            (B) LOCATION: 14
            (D) OTHER INFORMATION: /note= "Leu, Met or Phe"

(ix) FEATURE:
            (A) NAME/KEY: Modified-site
            (B) LOCATION: 15
            (D) OTHER INFORMATION: /note= "Gly or Glu"

(ix) FEATURE:
            (A) NAME/KEY: Modified-site
            (B) LOCATION: 16
            (D) OTHER INFORMATION: /note= "Ser or Pro"

(ix) FEATURE:
            (A) NAME/KEY: Modified-site
            (B) LOCATION: 19
            (D) OTHER INFORMATION: /note= "Ala or Pro"

(ix) FEATURE:
            (A) NAME/KEY: Modified-site
            (B) LOCATION: 22
            (D) OTHER INFORMATION: /note= "Ala or Val"

(ix) FEATURE:
            (A) NAME/KEY: Modified-site
            (B) LOCATION: 23
            (D) OTHER INFORMATION: /note= "Lys, Arg or Ala"
            (A) NAME/KEY: Modified-site
            (B) LOCATION: 27
            (D) OTHER INFORMATION: /note= "Ala or Thr"

(ix) FEATURE:
            (A) NAME/KEY: Modified-site
            (B) LOCATION: 31
            (D) OTHER INFORMATION: /note= "Tyr or Phe"

(ix) FEATURE:
            (A) NAME/KEY: Modified-site
            (B) LOCATION: 34
            (D) OTHER INFORMATION: /note= "Ile or Val"

(ix) FEATURE:
            (A) NAME/KEY: Modified-site
            (B) LOCATION: 35
            (D) OTHER INFORMATION: /note= "Lys or Gln"

(xi) SEQUENCE DESCRIPTION: SEQ ID NO:15:

Cys Lys Tyr Xaa Xaa Xaa Gly Xaa Xaa Xaa Arg Gly
1               5                   10

Asp Xaa Xaa Xaa Leu Ala Xaa Arg Val Xaa Xaa Cys
        15                  20

Leu Pro Xaa Ser Phe Asn Xaa Gly Ala Xaa Xaa
25              30                  35

(2) INFORMATION FOR SEQ ID NO:16:

(i) SEQUENCE CHARACTERISTICS:
            (A) LENGTH: 34 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
```

```
        (D) OTHER INFORMATION: /note= "Asn, Ser or Gly"

(ix) FEATURE:
     (A) NAME/KEY: Modified-site
     (B) LOCATION: 2
     (D) OTHER INFORMATION: /note= "Lys or Arg"

(ix) FEATURE:
     (A) NAME/KEY: Modified-site
     (B) LOCATION: 3
     (D) OTHER INFORMATION: /note= "Tyr or Ser"

(ix) FEATURE:
     (A) NAME/KEY: Modified-site
     (B) LOCATION: 4
     (D) OTHER INFORMATION: /note= "Ser or Pro"

(ix) FEATURE:
     (A) NAME/KEY: Modified-site
     (B) LOCATION: 5
     (D) OTHER INFORMATION: /note= "Thr, Ala, Pro, Arg,
         Ser or Asn"

(ix) FEATURE:
     (A) NAME/KEY: Modified-site
     (B) LOCATION: 6
     (D) OTHER INFORMATION: /note= "Asp, Gly, Ser, Ala,
         Pro or Leu"

(ix) FEATURE:
     (A) NAME/KEY: Modified-site
     (B) LOCATION: 7
     (D) OTHER INFORMATION: /note= "Gly, Asp or Arg"

(ix) FEATURE:
     (A) NAME/KEY: Modified-site
     (B) LOCATION: 8
     (D) OTHER INFORMATION: /note= "Pro, Ser, Arg, Thr,
         Val, Gln or Leu"

(ix) FEATURE:
     (A) NAME/KEY: Modified-site
     (B) LOCATION: 9
     (D) OTHER INFORMATION: /note= "Arg, Gly or Tyr"

(ix) FEATURE:
     (A) NAME/KEY: Modified-site
     (B) LOCATION: 10
     (D) OTHER INFORMATION: /note= "Arg, Ser, Ala, Gly
         or Pro"

(ix) FEATURE:
     (A) NAME/KEY: Modified-site
     (B) LOCATION: 11
     (D) OTHER INFORMATION: /note= "Gly or Asp"

(ix) FEATURE:
     (A) NAME/KEY: Modified-site
     (B) LOCATION: 12
     (D) OTHER INFORMATION: /note= "Asp or Pro"

(ix) FEATURE:
     (A) NAME/KEY: Modified-site
     (B) LOCATION: 13
     (D) OTHER INFORMATION: /note= "Leu, Met, Thr or
         Arg"

(ix) FEATURE:
     (A) NAME/KEY: Modified-site
     (B) LOCATION: 14
     (D) OTHER INFORMATION: /note= "Gly, Pro or Trp"

(ix) FEATURE:
     (A) NAME/KEY: Modified-site
     (B) LOCATION: 15
     (D) OTHER INFORMATION: /note= "Ser, Pro, Ala or
         Arg"

(ix) FEATURE:
```

(A) NAME/KEY: Modified-site
            (B) LOCATION: 16
            (D) OTHER INFORMATION: /note= "Leu, Pro, Thr or
                Ile"

(ix) FEATURE:
            (A) NAME/KEY: Modified-site
            (B) LOCATION: 17
            (D) OTHER INFORMATION: /note= "Ala, Thr, Leu, Arg
                or Ile"

(ix) FEATURE:
            (A) NAME/KEY: Modified-site
            (B) LOCATION: 18
            (D) OTHER INFORMATION: /note= "Ala, Gly, Thr or
                Gln"

(ix) FEATURE:
            (A) NAME/KEY: Modified-site
            (B) LOCATION: 19
            (D) OTHER INFORMATION: /note= "Arg, Glu or Lys"

(ix) FEATURE:
            (A) NAME/KEY: Modified-site
            (B) LOCATION: 20
            (D) OTHER INFORMATION: /note= "Ala, Val, Asp, Thr
                or Tyr"

(ix) FEATURE:
            (A) NAME/KEY: Modified-site
            (B) LOCATION: 21
            (D) OTHER INFORMATION: /note= "Ala or Arg"

(ix) FEATURE:
            (A) NAME/KEY: Modified-site
            (B) LOCATION: 22
            (D) OTHER INFORMATION: /note= "Lys, Thr, Arg or
                Ala"

(ix) FEATURE:
            (A) NAME/KEY: Modified-site
            (B) LOCATION: 24
            (D) OTHER INFORMATION: /note= "Leu or Pro"

(ix) FEATURE:
            (A) NAME/KEY: Modified-site
            (B) LOCATION: 25
            (D) OTHER INFORMATION: /note= "Pro or Ser"

(ix) FEATURE:
            (A) NAME/KEY: Modified-site
            (B) LOCATION: 26
            (D) OTHER INFORMATION: /note= "Ala or Thr"

(ix) FEATURE:
            (A) NAME/KEY: Modified-site
            (B) LOCATION: 30
            (D) OTHER INFORMATION: /note= "Tyr or Phe"

(ix) FEATURE:
            (A) NAME/KEY: Modified-site
            (B) LOCATION: 33
            (D) OTHER INFORMATION: /note= "Ile or Val"

(ix) FEATURE:
            (A) NAME/KEY: Modified-site
            (B) LOCATION: 34
            (D) OTHER INFORMATION: /note= "Arg, Lys or Gln"

(xi) SEQUENCE DESCRIPTION: SEQ ID NO:16:

Xaa Xaa Xaa Xaa Xaa Xaa Xaa Xaa Xaa Xaa Xaa Xaa
1               5                   10

Xaa Xaa Xaa Xaa Xaa Xaa Xaa Xaa Xaa Xaa Gln Xaa
            15                  20

Xaa Xaa Ser Phe Asn Xaa Gly Ala Xaa Xaa
25              30

(2) INFORMATION FOR SEQ ID NO:17:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Lyr or Arg"

(ix) FEATURE:
        (A) NAME/KEY: Modified-site
        (B) LOCATION: 3
        (D) OTHER INFORMATION: /note= "Tyr or Ser"

(ix) FEATURE:
        (A) NAME/KEY: Modified-site
        (B) LOCATION: 4
        (D) OTHER INFORMATION: /note= "Ser or Pro"

(ix) FEATURE:
        (A) NAME/KEY: Modified-site
        (B) LOCATION: 5
        (D) OTHER INFORMATION: /note= "Thr, Ala, Pro, Arg,
           Ser or Asn"

(ix) FEATURE:
        (A) NAME/KEY: Modified-site
        (B) LOCATION: 6
        (D) OTHER INFORMATION: /note= "Asp, Gly, Ser, Ala,
           Pro or Leu"

(ix) FEATURE:
        (A) NAME/KEY: Modified-site
        (B) LOCATION: 7
        (D) OTHER INFORMATION: /note= "Gly, Asp or Arg"

(ix) FEATURE:
        (A) NAME/KEY: Modified-site
        (B) LOCATION: 8
        (D) OTHER INFORMATION: /note= "Pro, Ser, Arg, Thr,
           Val, Gln or Leu"

(ix) FEATURE:
        (A) NAME/KEY: Modified-site
        (B) LOCATION: 9
        (D) OTHER INFORMATION: /note= "Arg, Gly or Tyr"

(ix) FEATURE:
        (A) NAME/KEY: Modified-site
        (B) LOCATION: 10
        (D) OTHER INFORMATION: /note= "Arg, Ser, Ala, Gly
           or Pro"

(ix) FEATURE:
        (A) NAME/KEY: Modified-site
        (B) LOCATION: 11
        (D) OTHER INFORMATION: /note= "Gly or Asp"

(ix) FEATURE:
        (A) NAME/KEY: Modified-site
        (B) LOCATION: 12
        (D) OTHER INFORMATION: /note= "Asp or Pro"

(ix) FEATURE:
        (A) NAME/KEY: Modified-site
        (B) LOCATION: 13
        (D) OTHER INFORMATION: /note= "Leu, Met, Thr or
           Arg"

(ix) FEATURE:
        (A) NAME/KEY: Modified-site
        (B) LOCATION: 14

```
          (D) OTHER INFORMATION: /note= "Gly, Pro or Trp"

(ix) FEATURE:
          (A) NAME/KEY: Modified-site
          (B) LOCATION: 15
          (D) OTHER INFORMATION: /note= "Ser, Pro, Ala or
              Arg"

(ix) FEATURE:
          (A) NAME/KEY: Modified-site
          (B) LOCATION: 16
          (D) OTHER INFORMATION: /note= "Leu, Pro, Thr or
              Ile"

(ix) FEATURE:
          (A) NAME/KEY: Modified-site
          (B) LOCATION: 17
          (D) OTHER INFORMATION: /note= "Ala, Thr, Leu, Arg
              or Ile"

(ix) FEATURE:
          (A) NAME/KEY: Modified-site
          (B) LOCATION: 18
          (D) OTHER INFORMATION: /note= "Ala, Gly, Thr or
              Gln"

(ix) FEATURE:
          (A) NAME/KEY: Modified-site
          (B) LOCATION: 19
          (D) OTHER INFORMATION: /note= "Arg, Glu or Lys"

(ix) FEATURE:
          (A) NAME/KEY: Modified-site
          (B) LOCATION: 20
          (D) OTHER INFORMATION: /note= "Ala, Val, Asp, Thr
              or Tyr"

(ix) FEATURE:
          (A) NAME/KEY: Modified-site
          (B) LOCATION: 21
          (D) OTHER INFORMATION: /note= "Ala or Arg"

(ix) FEATURE:
          (A) NAME/KEY: Modified-site
          (B) LOCATION: 22
          (D) OTHER INFORMATION: /note= "Lys, Thr, Arg or
              Ala"

(ix) FEATURE:
          (A) NAME/KEY: Modified-site
          (B) LOCATION: 24
          (D) OTHER INFORMATION: /note= "Leu or Pro"

(ix) FEATURE:
          (A) NAME/KEY: Modified-site
          (B) LOCATION: 25
          (D) OTHER INFORMATION: /note= "Pro or Ser"

(ix) FEATURE:
          (A) NAME/KEY: Modified-site
          (B) LOCATION: 26
          (D) OTHER INFORMATION: /note= "Ala or Thr"

(ix) FEATURE:
          (A) NAME/KEY: Modified-site
          (B) LOCATION: 30
          (D) OTHER INFORMATION: /note= "Tyr or Phe"

(ix) FEATURE:
          (A) NAME/KEY: Modified-site
          (B) LOCATION: 33
          (D) OTHER INFORMATION: /note= "Ile or Val"

(ix) FEATURE:
          (A) NAME/KEY: Modified-site
          (B) LOCATION: 34
          (D) OTHER INFORMATION: /note= "Arg, Lys or Gln"

(xi) SEQUENCE DESCRIPTION: SEQ ID NO:17:
```

```
Cys Xaa Xaa Xaa Xaa Xaa Xaa Xaa Xaa Xaa Xaa
1               5                   10

Xaa Xaa Xaa Xaa Xaa Xaa Xaa Xaa Xaa Xaa Cys Xaa
            15                  20

Xaa Xaa Ser Phe Asn Xaa Gly Ala Xaa Xaa
25                  30
```

(2) INFORMATION FOR SEQ ID NO:18:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Cys or Ser"

(ix) FEATURE:
        (A) NAME/KEY: Modified-site
        (B) LOCATION: 2
        (D) OTHER INFORMATION: /note= "Lys, Arg or Gln"

(ix) FEATURE:
        (A) NAME/KEY: Modified-site
        (B) LOCATION: 4
        (D) OTHER INFORMATION: /note= "Gly, Ser or Asn"

(ix) FEATURE:
        (A) NAME/KEY: Modified-site
        (B) LOCATION: 5
        (D) OTHER INFORMATION: /note= "Glu, Ser, Asp, Thr,
           Lys or Asn"

(ix) FEATURE:
        (A) NAME/KEY: Modified-site
        (B) LOCATION: 6
        (D) OTHER INFORMATION: /note= "Asn, Ser, Gly, Val
           or Trp"

(ix) FEATURE:
        (A) NAME/KEY: Modified-site
        (B) LOCATION: 7
        (D) OTHER INFORMATION: /note= "Ala, Ser, Thr or
           Gly"

(ix) FEATURE:
        (A) NAME/KEY: Modified-site
        (B) LOCATION: 9
        (D) OTHER INFORMATION: /note= "Thr, Pro or Ala"

(ix) FEATURE:
        (A) NAME/KEY: Modified-site
        (B) LOCATION: 10
        (D) OTHER INFORMATION: /note= "Asn or Ala"

(ix) FEATURE:
        (A) NAME/KEY: Modified-site
        (B) LOCATION: 11
        (D) OTHER INFORMATION: /note= "Val, Ile or Leu"

(ix) FEATURE:
        (A) NAME/KEY: Modified-site
        (B) LOCATION: 15
        (D) OTHER INFORMATION: /note= "Leu, Pro or Gln"

(ix) FEATURE:
        (A) NAME/KEY: Modified-site
        (B) LOCATION: 16
        (D) OTHER INFORMATION: /note= "Gln or Asn"

(ix) FEATURE:

(A) NAME/KEY: Modified-site
            (B) LOCATION: 17
            (D) OTHER INFORMATION: /note= "Val, Ala or Leu"

(ix) FEATURE:
            (A) NAME/KEY: Modified-site
            (B) LOCATION: 19
            (D) OTHER INFORMATION: /note= "Ala, Glu or Ser"

(ix) FEATURE:
            (A) NAME/KEY: Modified-site
            (B) LOCATION: 20
            (D) OTHER INFORMATION: /note= "Gln or Arg"

(ix) FEATURE:
            (A) NAME/KEY: Modified-site
            (B) LOCATION: 22
            (D) OTHER INFORMATION: /note= "Ala or Val"

(ix) FEATURE:
            (A) NAME/KEY: Modified-site
            (B) LOCATION: 23
            (D) OTHER INFORMATION: /note= "Ala or Glu"

(ix) FEATURE:
            (A) NAME/KEY: Modified-site
            (B) LOCATION: 25
            (D) OTHER INFORMATION: /note= "Thr, Ala or Met"

(ix) FEATURE:
            (A) NAME/KEY: Modified-site
            (B) LOCATION: 28
            (D) OTHER INFORMATION: /note= "Thr or Ala"

(ix) FEATURE:
            (A) NAME/KEY: Modified-site
            (B) LOCATION: 29
            (D) OTHER INFORMATION: /note= "Ser or Tyr"

(ix) FEATURE:
            (A) NAME/KEY: Modified-site
            (B) LOCATION: 36
            (D) OTHER INFORMATION: /note= "Lyr or Arg"

(xi) SEQUENCE DESCRIPTION: SEQ ID NO:18:

Xaa Xaa Tyr Xaa Xaa Xaa Xaa Val Xaa Xaa Xaa Arg
1               5                   10

Gly Asp Xaa Xaa Xaa Leu Xaa Xaa Lys Xaa Xaa Arg
        15                  20

Xaa Leu Pro Xaa Xaa Phe Asn Tyr Gly Ala Ile Xaa
25              30                  35

(2) INFORMATION FOR SEQ ID NO:19:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "Lys, Arg or Gln"

(ix) FEATURE:
            (A) NAME/KEY: Modified-site
            (B) LOCATION: 4
            (D) OTHER INFORMATION: /note= "Gly, Ser or Asn"

(ix) FEATURE:
            (A) NAME/KEY: Modified-site
            (B) LOCATION: 5
            (D) OTHER INFORMATION: /note= "Glu, Ser, Asp, Lys or Asn"

(ix) FEATURE:
    (A) NAME/KEY: Modified-site
    (B) LOCATION: 6
    (D) OTHER INFORMATION: /note= "Asn, Ser, Gly, or
        Trp"

(ix) FEATURE:
    (A) NAME/KEY: Modified-site
    (B) LOCATION: 7
    (D) OTHER INFORMATION: /note= "Ala, Ser, or Thr"

(ix) FEATURE:
    (A) NAME/KEY: Modified-site
    (B) LOCATION: 9
    (D) OTHER INFORMATION: /note= "Thr, Pro or Ala"

(ix) FEATURE:
    (A) NAME/KEY: Modified-site
    (B) LOCATION: 10
    (D) OTHER INFORMATION: /note= "Asn or Ala"

(ix) FEATURE:
    (A) NAME/KEY: Modified-site
    (B) LOCATION: 11
    (D) OTHER INFORMATION: /note= "Val, Ile or Leu"

(ix) FEATURE:
    (A) NAME/KEY: Modified-site
    (B) LOCATION: 15
    (D) OTHER INFORMATION: /note= "Leu, Pro or Gln"

(ix) FEATURE:
    (A) NAME/KEY: Modified-site
    (B) LOCATION: 16
    (D) OTHER INFORMATION: /note= "Gln or Asn"

(ix) FEATURE:
    (A) NAME/KEY: Modified-site
    (B) LOCATION: 17
    (D) OTHER INFORMATION: /note= "Val, Ala or Leu"

(ix) FEATURE:
    (A) NAME/KEY: Modified-site
    (B) LOCATION: 19
    (D) OTHER INFORMATION: /note= "Ala, Glu or Ser"

(ix) FEATURE:
    (A) NAME/KEY: Modified-site
    (B) LOCATION: 20
    (D) OTHER INFORMATION: /note= "Gln or Arg"

(ix) FEATURE:
    (A) NAME/KEY: Modified-site
    (B) LOCATION: 22
    (D) OTHER INFORMATION: /note= "Ala or Val"

(ix) FEATURE:
    (A) NAME/KEY: Modified-site
    (B) LOCATION: 23
    (D) OTHER INFORMATION: /note= "Ala or Glu"

(ix) FEATURE:
    (A) NAME/KEY: Modified-site
    (B) LOCATION: 25
    (D) OTHER INFORMATION: /note= "Thr, Ala or Met"

(ix) FEATURE:
    (A) NAME/KEY: Modified-site
    (B) LOCATION: 28
    (D) OTHER INFORMATION: /note= "Thr or Ala"

(ix) FEATURE:
    (A) NAME/KEY: Modified-site
    (B) LOCATION: 29
    (D) OTHER INFORMATION: /note= "Ser or Tyr"

(ix) FEATURE:

(A) NAME/KEY: Modified-site
            (B) LOCATION: 36
            (D) OTHER INFORMATION: /note= "Lyr or Arg"

(xi) SEQUENCE DESCRIPTION: SEQ ID NO:19:

Cys Xaa Tyr Xaa Xaa Xaa Xaa Val Xaa Xaa Xaa Arg
1               5                   10

Gly Asp Xaa Xaa Xaa Leu Xaa Xaa Lys Xaa Xaa Arg
            15                  20

Xaa Leu Pro Xaa Xaa Phe Asn Tyr Gly Ala Ile Xaa
25                  30                  35

(2) INFORMATION FOR SEQ ID NO:20:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Thr, Pro or Arg"

(ix) FEATURE:
        (A) NAME/KEY: Modified-site
        (B) LOCATION: 2
        (D) OTHER INFORMATION: /note= "Thr or Pro"

(ix) FEATURE:
        (A) NAME/KEY: Modified-site
        (B) LOCATION: 5
        (D) OTHER INFORMATION: /note= "Thr, Glu or Lys"

(ix) FEATURE:
        (A) NAME/KEY: Modified-site
        (B) LOCATION: 6
        (D) OTHER INFORMATION: /note= "Gln or Thr"

(ix) FEATURE:
        (A) NAME/KEY: Modified-site
        (B) LOCATION: 7
        (D) OTHER INFORMATION: /note= "Pro or Thr"

(ix) FEATURE:
        (A) NAME/KEY: Modified-site
        (B) LOCATION: 8
        (D) OTHER INFORMATION: /note= "Ser or Thr"

(ix) FEATURE:
        (A) NAME/KEY: Modified-site
        (B) LOCATION: 13
        (D) OTHER INFORMATION: /note= "Met or Leu"

(ix) FEATURE:
        (A) NAME/KEY: Modified-site
        (B) LOCATION: 15
        (D) OTHER INFORMATION: /note= "Ala or Val"

(ix) FEATURE:
        (A) NAME/KEY: Modified-site
        (B) LOCATION: 20
        (D) OTHER INFORMATION: /note= "Leu or Val"

(ix) FEATURE:
        (A) NAME/KEY: Modified-site
        (B) LOCATION: 22
        (D) OTHER INFORMATION: /note= "Arg, Asn or Ala"

(ix) FEATURE:
        (A) NAME/KEY: Modified-site
        (B) LOCATION: 23
        (D) OTHER INFORMATION: /note= "Arg or Gln"

(xi) SEQUENCE DESCRIPTION: SEQ ID NO:20:

Xaa Xaa Tyr Gly Xaa Xaa Xaa Xaa Arg Arg Gly Asp
1               5                   10

Xaa Ala Xaa Leu Ala Gln Arg Xaa Ser Xaa Xaa Leu
            15                  20

Pro Thr Ser Phe Asn Tyr Gly Ala Val Lys
25                  30

(2) INFORMATION FOR SEQ ID NO:21:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Thr or Pro"

(ix) FEATURE:
        (A) NAME/KEY: Modified-site
        (B) LOCATION: 5
        (D) OTHER INFORMATION: /note= "Thr, Glu or Lys"

(ix) FEATURE:
        (A) NAME/KEY: Modified-site
        (B) LOCATION: 6
        (D) OTHER INFORMATION: /note= "Gln or Thr"

(ix) FEATURE:
        (A) NAME/KEY: Modified-site
        (B) LOCATION: 7
        (D) OTHER INFORMATION: /note= "Pro or Thr"

(ix) FEATURE:
        (A) NAME/KEY: Modified-site
        (B) LOCATION: 8
        (D) OTHER INFORMATION: /note= "Ser or Thr"

(ix) FEATURE:
        (A) NAME/KEY: Modified-site
        (B) LOCATION: 13
        (D) OTHER INFORMATION: /note= "Met or Leu"

(ix) FEATURE:
        (A) NAME/KEY: Modified-site
        (B) LOCATION: 15
        (D) OTHER INFORMATION: /note= "Ala or Val"

(ix) FEATURE:
        (A) NAME/KEY: Modified-site
        (B) LOCATION: 20
        (D) OTHER INFORMATION: /note= "Leu or Val"

(ix) FEATURE:
        (A) NAME/KEY: Modified-site
        (B) LOCATION: 22
        (D) OTHER INFORMATION: /note= "Arg, Asn or Ala"

(xi) SEQUENCE DESCRIPTION: SEQ ID NO:21:

Cys Xaa Tyr Gly Xaa Xaa Xaa Xaa Arg Arg Gly Asp
1               5                   10

Xaa Ala Xaa Leu Ala Gln Arg Xaa Ser Xaa Cys Leu
            15                  20

Pro Thr Ser Phe Asn Tyr Gly Ala Val Lys
25                  30

(2) INFORMATION FOR SEQ ID NO:22:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:22:

Thr Ala Lys Ser Lys Lys Phe Pro Ser Tyr Thr Ala
1               5                   10
Thr Tyr Gln Phe
            15

(2) INFORMATION FOR SEQ ID NO:23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:23:

Pro Pro Xaa Pro Xaa Pro
1               5

(2) INFORMATION FOR SEQ ID NO:24:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:24:

Glu Thr Gln Ile Gln Arg Arg Gln His Thr Asp Val
1               5                   10
Ser Phe Ile Met Asp Arg Phe Val
            15                  20

(2) INFORMATION FOR SEQ ID NO:25:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:25:

Lys Lys Lys Ile Ile Thr Ile Thr Arg Ile Ile Thr
1               5                   10
Ile Ile Thr Thr Ile Asp
            15

(2) INFORMATION FOR SEQ ID NO:26:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:

(A) NAME/KEY: Modified-site
                (B) LOCATION: 4
                (D) OTHER INFORMATION: /note= "Ser or Thr"

(ix) FEATURE:
                (A) NAME/KEY: Modified-site
                (B) LOCATION: 7
                (D) OTHER INFORMATION: /note= "Lyr or Arg"

(ix) FEATURE:
                (A) NAME/KEY: Modified-site
                (B) LOCATION: 8
                (D) OTHER INFORMATION: /note= "Gly or Thr"

(ix) FEATURE:
                (A) NAME/KEY: Modified-site
                (B) LOCATION: 12
                (D) OTHER INFORMATION: /note= "His or Thr"

(ix) FEATURE:
                (A) NAME/KEY: Modified-site
                (B) LOCATION: 13
                (D) OTHER INFORMATION: /note= "Lys or Arg"

(ix) FEATURE:
                (A) NAME/KEY: Modified-site
                (B) LOCATION: 16
                (D) OTHER INFORMATION: /note= "Gly or Thr"

(xi) SEQUENCE DESCRIPTION: SEQ ID NO:26:

Ile Ser Ile Xaa Glu Ile Xaa Xaa Val Ile Val Xaa
1               5                   10

Xaa Ile Glu Xaa Ile Leu Phe
            15

(2) INFORMATION FOR SEQ ID NO:27:

(i) SEQUENCE CHARACTERISTICS:
                (A) LENGTH: 65 amino acids
                (B) TYPE: amino acid
                (D) TOPOLOGY: linear (ii) MOLECULE TYPE: peptide (xi) SEQUENCE DESCRIPTION: SEQ ID NO:27:

Thr Ala Lys Ser Lys Lys Phe Pro Ser Tyr Thr Ala
1               5                   10

Thr Tyr Gln Phe Gly Gly Glu Thr Gln Ile Gln Arg
            15                  20

Arg Gln His Thr Asp Val Ser Phe Ile Met Asp Arg
25                  30                  35

Phe Val Gly Gly Cys Lys Tyr Ser Ala Ser Gly Ser
                40                  45

Gly Val Arg Gly Asp Phe Gly Ser Leu Ala Pro Arg
    50                  55                  60

Val Ala Arg Cys Leu
                65

(2) INFORMATION FOR SEQ ID NO:28:

(i) SEQUENCE CHARACTERISTICS:
                (A) LENGTH: 75 amino acids
                (B) TYPE: amino acid
                (D) TOPOLOGY: linear (ii) MOLECULE TYPE: peptide (xi) SEQUENCE DESCRIPTION: SEQ ID NO:28:

```
Thr Ala Lys Ser Lys Lys Phe Pro Ser Tyr Thr Ala
1               5                   10

Thr Tyr Gln Phe Gly Gly Glu Thr Gln Ile Gln Arg
            15              20

Arg Gln His Thr Asp Val Ser Phe Ile Met Asp Arg
25              30                  35

Phe Val Gly Gly Asn Lys Tyr Ser Ala Ser Gly Ser
            40              45

Gly Val Arg Gly Asp Phe Gly Ser Leu Ala Pro Arg
    50              55                  60

Val Ala Arg Gln Leu Pro Ala Ser Phe Asn Tyr Gly
            65              70

Ala Ile Lys
    75
```

(2) INFORMATION FOR SEQ ID NO:29:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO:29:

```
Thr Ala Lys Ser Lys Lys Phe Pro Ser Tyr Thr Ala
1               5                   10

Thr Tyr Gln Phe Gly Gly Glu Thr Gln Ile Gln Arg
            15              20

Arg Gln His Thr Asp Val Ser Phe Ile Met Asp Arg
25              30                  35

Phe Val Gly Gly Cys Lys Tyr Ser Ala Ser Gly Ser
            40              45

Gly Val Arg Gly Asp Phe Gly Ser Leu Ala Pro Arg
    50              55                  60

Val Ala Arg Cys Leu Pro Ala Ser Phe Asn Tyr Gly
            65              70

Ala Ile Lys
    75
```

(2) INFORMATION FOR SEQ ID NO:30:

(i) SEQUENCE CHARACTERISTICS:
        (A) LENGTH: 80 amino acids
        (B) TYPE: amino acid
        (D) TOPOLOGY: linear (ii) MOLECULE TYPE: peptide (xi) SEQUENCE DESCRIPTION: SEQ ID NO:30:

```
Thr Ala Lys Ser Lys Lys Phe Pro Ser Tyr Thr Ala
1               5                   10

Thr Tyr Gln Phe Gly Gly Ile Ser Ile Ser Glu Ile
            15              20

Lys Gly Val Ile Val His Lys Ile Glu Gly Ile Leu
25              30                  35

Phe Gly Gly Val Tyr Asn Gly Asn Cys Lys Tyr Gly
            40              45

Glu Asn Ala Val Thr Asn Val Arg Gly Asp Leu Gln
```

```
            50                  55                  60
Val Leu Ala Gln Lys Ala Ala Arg Cys Leu Pro Thr
                65                  70

Ser Phe Asn Tyr Gly Ala Ile Lys
        75                  80
```

(2) INFORMATION FOR SEQ ID NO:31:

(i) SEQUENCE CHARACTERISTICS:
        (A) LENGTH: 56 amino acids
        (B) TYPE: amino acid
        (D) TOPOLOGY: linear (ii) MOLECULE TYPE: peptide (xi) SEQUENCE DESCRIPTION: SEQ ID NO:31:

```
Lys Lys Lys Ile Ile Thr Ile Thr Arg Ile Ile Thr
1               5                   10

Ile Ile Thr Thr Ile Asp Gly Gly Cys Lys Tyr Gly
            15                  20

Glu Asn Ala Val Thr Asn Val Arg Gly Asp Leu Gln
25                  30                  35

Val Leu Ala Gln Lys Ala Ala Arg Cys Leu Pro Thr
                40                  45

Ser Phe Asn Tyr Gly Ala Ile Lys
        50                  55
```

(2) INFORMATION FOR SEQ ID NO:32:

(i) SEQUENCE CHARACTERISTICS:
        (A) LENGTH: 72 amino acids
        (B) TYPE: amino acid
        (D) TOPOLOGY: linear (ii) MOLECULE TYPE: peptide (xi) SEQUENCE DESCRIPTION: SEQ ID NO:32:

```
Thr Ala Lys Ser Lys Lys Phe Pro Ser Tyr Thr Ala
1               5                   10

Thr Tyr Gln Phe Gly Gly Lys Lys Lys Ile Ile Thr
            15                  20

Ile Thr Arg Ile Ile Thr Ile Ile Thr Thr Ile Asp
25                  30                  35

Gly Gly Cys Thr Tyr Gly Thr Gln Pro Ser Arg Arg
            40                  45

Gly Asp Met Ala Ala Leu Ala Gln Arg Leu Ser Arg
        50                  55                  60

Cys Leu Pro Thr Ser Phe Asn Tyr Gly Ala Val Lys
                65                  70
```

(2) INFORMATION FOR SEQ ID NO:33:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (xi) SEQUENCE DESCRIPTION: SEQ ID NO:33:

```
Lys Lys Lys Ile Ile Thr Ile Thr Arg Ile Ile Thr
1               5                   10
```

```
Ile Ile Thr Thr Ile Asp Gly Gly Cys Lys Tyr Ser
        15                  20

Val Ser Gly Ser Gly Arg Arg Gly Asp Leu Gly Ser
25              30                  35

Leu Ala Ala Arg Val Ala Lys Cys Leu Pro Ala Ser
            40              45

Phe Asn Tyr Gly Ala Ile Lys
50                  55
```

FORMATION FOR SEQ ID NO:34:

(i) SEQUENCE CHARACTERISTICS:
        (A) LENGTH: 54 amino acids
        (B) TYPE: amino acid
        (D) TOPOLOGY: linear (ii) MOLECULE TYPE: peptide (xi) SEQUENCE DESCRIPTION: SEQ ID NO:34:

```
Lys Lys Lys Ile Ile Thr Ile Thr Arg Ile Ile Thr
1               5                   10

Ile Ile Thr Thr Ile Asp Gly Gly Cys Lys Tyr Ser
        15                  20

Thr Asp Gly Pro Arg Arg Gly Asp Met Gly Ser Leu
25              30                  35

Ala Ala Arg Ala Ala Lys Cys Leu Pro Ala Ser Phe
            40              45

Asn Tyr Gly Ala Ile Arg
    50
```

FORMATION FOR SEQ ID NO:35:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Lys, Thr, Pro or
            Arg"

(ix) FEATURE:
        (A) NAME/KEY: Modified-site
        (B) LOCATION: 3
        (D) OTHER INFORMATION: /note= "Tyr or Ser"

(ix) FEATURE:
        (A) NAME/KEY: Modified-site
        (B) LOCATION: 4
        (D) OTHER INFORMATION: /note= "Ser, Gly or Pro"

(ix) FEATURE:
        (A) NAME/KEY: Modified-site
        (B) LOCATION: 5
        (D) OTHER INFORMATION: /note= "Thr, Ala, Glu, Lys,
            Asn, Pro, Arg or Ser"

(ix) FEATURE:
        (A) NAME/KEY: Modified-site
        (B) LOCATION: 6
        (D) OTHER INFORMATION: /note= "Asp, Gly, Gln, Ser,
            Ala, Pro, Leu or Thr"

(ix) FEATURE:

```
                  (A) NAME/KEY: Modified-site
                  (B) LOCATION: 7
                  (D) OTHER INFORMATION: /note= "Gly, Pro, Asp, Arg
                        or Thr"

(ix) FEATURE:
                  (A) NAME/KEY: Modified-site
                  (B) LOCATION: 8
                  (D) OTHER INFORMATION: /note= "Pro, Ser, Thr, Arg,
                        Val, Gln or Leu"

(ix) FEATURE:
                  (A) NAME/KEY: Modified-site
                  (B) LOCATION: 9
                  (D) OTHER INFORMATION: /note= "Arg, Gly or Tyr"

(ix) FEATURE:
                  (A) NAME/KEY: Modified-site
                  (B) LOCATION: 10
                  (D) OTHER INFORMATION: /note= "Arg, Ser, Ala, Gly
                        or Pro"

(ix) FEATURE:
                  (A) NAME/KEY: Modified-site
                  (B) LOCATION: 11
                  (D) OTHER INFORMATION: /note= "Gly or Asp"

(ix) FEATURE:
                  (A) NAME/KEY: Modified-site
                  (B) LOCATION: 12
                  (D) OTHER INFORMATION: /note= "Asp or Pro"

(ix) FEATURE:
                  (A) NAME/KEY: Modified-site
                  (B) LOCATION: 13
                  (D) OTHER INFORMATION: /note= "Met, Leu, Thr or
                        Arg"

(ix) FEATURE:
                  (A) NAME/KEY: Modified-site
                  (B) LOCATION: 14
                  (D) OTHER INFORMATION: /note= "Gly, Ala, Pro or
                        Trp"

(ix) FEATURE:
                  (A) NAME/KEY: Modified-site
                  (B) LOCATION: 15
                  (D) OTHER INFORMATION: /note= "Ser, Pro, Ala, Val
                        or Arg"

(ix) FEATURE:
                  (A) NAME/KEY: Modified-site
                  (B) LOCATION: 16
                  (D) OTHER INFORMATION: /note= "Leu, Pro, Thr or
                        Ile"

(ix) FEATURE:
                  (A) NAME/KEY: Modified-site
                  (B) LOCATION: 17
                  (D) OTHER INFORMATION: /note= Ala, Thr, Leu, Ile
                        or Arg"

(ix) FEATURE:
                  (A) NAME/KEY: Modified-site
                  (B) LOCATION: 18
                  (D) OTHER INFORMATION: /note= "Ala, Gln, Gly or
                        Thr"

(ix) FEATURE:
                  (A) NAME/KEY: Modified-site
                  (B) LOCATION: 19
                  (D) OTHER INFORMATION: /note= "Arg, Glu or Lys"

(ix) FEATURE:
                  (A) NAME/KEY: Modified-site
                  (B) LOCATION: 20
                  (D) OTHER INFORMATION: /note= "Ala, Val, Leu, Asp,
                        Thr or Tyr"
```

(ix) FEATURE:
        (A) NAME/KEY: Modified-site
        (B) LOCATION: 21
        (D) OTHER INFORMATION: /note= "Ala, Ser or Arg"

(ix) FEATURE:
        (A) NAME/KEY: Modified-site
        (B) LOCATION: 22
        (D) OTHER INFORMATION: /note= "Lys, Arg, Thr, Asn
            or Ala"

(ix) FEATURE:
        (A) NAME/KEY: Modified-site
        (B) LOCATION: 24
        (D) OTHER INFORMATION: /note= "Leu, Pro or Thr"

(ix) FEATURE:
        (A) NAME/KEY: Modified-site
        (B) LOCATION: 25
        (D) OTHER INFORMATION: /note= "Pro or Ser"

(ix) FEATURE:
        (A) NAME/KEY: Modified-site
        (B) LOCATION: 26
        (D) OTHER INFORMATION: /note= "Ala or Thr"

(ix) FEATURE:
        (A) NAME/KEY: Modified-site
        (B) LOCATION: 30
        (D) OTHER INFORMATION: /note= "Tyr or Phe"

(ix) FEATURE:
        (A) NAME/KEY: Modified-site
        (B) LOCATION: 33
        (D) OTHER INFORMATION: /note= "Ile or Val"

(ix) FEATURE:
        (A) NAME/KEY: Modified-site
        (B) LOCATION: 34
        (D) OTHER INFORMATION: /note= "Arg, Lys or Gln"

(xi) SEQUENCE DESCRIPTION: SEQ ID NO:35:

Cys Xaa Xaa Xaa Xaa Xaa Xaa Xaa Xaa Xaa Xaa Xaa
1               5                   10

Xaa Xaa Xaa Xaa Xaa Xaa Xaa Xaa Xaa Xaa Cys Xaa
        15                  20

Xaa Xaa Ser Phe Asn Xaa Gly Ala Xaa Xaa
25              30

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Ile, Met or Leu"

(ix) FEATURE:
        (A) NAME/KEY: Modified-site
        (B) LOCATION: 2
        (D) OTHER INFORMATION: /note= "Ser or Thr"

(ix) FEATURE:
        (A) NAME/KEY: Modified-site
        (B) LOCATION: 4
        (D) OTHER INFORMATION: /note= "Ile or Arg"

(ix) FEATURE:
        (A) NAME/KEY: Modified-site

```
        (B) LOCATION: 5
        (D) OTHER INFORMATION: /note= "Lys or Thr"

(ix) FEATURE:
        (A) NAME/KEY: Modified-site
        (B) LOCATION: 10
        (D) OTHER INFORMATION: /note= "His or Thr"

(ix) FEATURE:
        (A) NAME/KEY: Modified-site
        (B) LOCATION: 11
        (D) OTHER INFORMATION: /note= "Lys or Arg"

(ix) FEATURE:
        (A) NAME/KEY: Modified-site
        (B) LOCATION: 12
        (D) OTHER INFORMATION: /note= "Ile, Met or Leu"

(ix) FEATURE:
        (A) NAME/KEY: Modified-site
        (B) LOCATION: 14
        (D) OTHER INFORMATION: /note= "Gly or Thr"

(ix) FEATURE:
        (A) NAME/KEY: Modified-site
        (B) LOCATION: 15
        (D) OTHER INFORMATION: /note= "Ile, Met or Val"

(xi) SEQUENCE DESCRIPTION: SEQ ID NO:36:

Xaa Xaa Glu Xaa Xaa Gly Val Ile Val Xaa Xaa Xaa
1               5                   10

Glu Xaa Xaa
        15

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Ser or Thr"

(ix) FEATURE:
        (A) NAME/KEY: Modified-site
        (B) LOCATION: 5
        (D) OTHER INFORMATION: /note= "Lys or Arg"

(ix) FEATURE:
        (A) NAME/KEY: Modified-site
        (B) LOCATION: 6
        (D) OTHER INFORMATION: /note= "Gly or Thr"

(ix) FEATURE:
        (A) NAME/KEY: Modified-site
        (B) LOCATION: 10
        (D) OTHER INFORMATION: /note= "His or Thr"

(ix) FEATURE:
        (A) NAME/KEY: Modified-site
        (B) LOCATION: 11
        (D) OTHER INFORMATION: /note= "Lys or Arg"

(ix) FEATURE:
        (A) NAME/KEY: Modified-site
        (B) LOCATION: 14
        (D) OTHER INFORMATION: /note= "Gly or Thr"

(xi) SEQUENCE DESCRIPTION: SEQ ID NO:37:

Ile Xaa Glu Ile Xaa Xaa Val Ile Val Xaa Xaa Ile
```

```
1               5                   10
Glu Xaa Ile
        15
```

(2) INFORMATION FOR SEQ ID NO:38:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:38:

```
Val Leu Ala Thr Val Tyr Asn Gly Thr Asn Lys Tyr
1               5                   10

Ser Ala Ser Gly Ser Gly Val Arg Gly Asp Phe Gly
            15                  20

Ser Leu Ala Pro Arg Val Ala Arg Gln Leu Pro Ala
25                  30                  35

Ser Phe Asn Tyr Gly Ala Ile Lys Ala Glu
            40                  45
```

(2) INFORMATION FOR SEQ ID NO:39:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:39:

```
Val Leu Ala Thr Val Tyr Asn Gly Thr Ser Lys Tyr
1               5                   10

Ser Ala Gly Gly Thr Gly Arg Arg Gly Asp Leu Gly
            15                  20

Pro Leu Ala Ala Arg Val Ala Ala Gln Leu Pro Ala
25                  30                  35

Ser Phe Asn Phe Gly Ala Ile Gln Ala Thr
            40                  45
```

(2) INFORMATION FOR SEQ ID NO:40:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:40:

```
Val Leu Ala Thr Val Tyr Asn Gly Thr Gly Lys Tyr
1               5                   10

Ser Ala Gly Gly Met Gly Arg Arg Gly Asp Leu Glu
            15                  20

Pro Leu Ala Ala Arg Val Ala Ala Gln Leu Pro Ala
25                  30                  35

Ser Phe Asn Phe Gly Ala Ile Gln Ala Thr
            40                  45
```

(2) INFORMATION FOR SEQ ID NO:41:

(i) SEQUENCE CHARACTERISTICS:
    (A) LENGTH: 46 amino acids
    (B) TYPE: amino acid
    (D) TOPOLOGY: linear (ii) MOLECULE TYPE: peptide (xi) SEQUENCE DESCRIPTION: SEQ ID NO:41:

Val Leu Ala Thr Val Tyr Asn Gly Thr Ser Lys Tyr
1               5                  10

Ser Ala Gly Gly Met Gly Arg Arg Gly Asp Leu Glu
           15              20

Pro Leu Ala Ala Arg Val Ala Ala Gln Leu Pro Thr
25                  30                  35

Ser Phe Asn Phe Gly Ala Ile Gln Ala Thr
            40              45

(2) INFORMATION FOR SEQ ID NO:42:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:42:

Val Pro Ala Thr Val Tyr Asn Gly Thr Ser Lys Tyr
1               5                  10

Ala Val Gly Gly Ser Gly Arg Arg Gly Asp Met Gly
           15              20

Ser Leu Ala Ala Arg Val Ala Lys Gln Leu Pro Ala
25                  30                  35

Ser Phe Asn Tyr Gly Ala Ile Lys Ala Thr
            40              45

(2) INFORMATION FOR SEQ ID NO:43:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:43:

Val Ser Ala Thr Val Tyr Asn Gly Thr Ser Lys Tyr
1               5                  10

Ala Val Gly Gly Ser Gly Arg Arg Gly Asp Met Gly
           15              20

Ser Leu Ala Ala Arg Val Val Lys Gln Leu Pro Ala
25                  30                  35

Ser Phe Asn Tyr Gly Ala Ile Lys Ala Asp
            40              45

(2) INFORMATION FOR SEQ ID NO:44:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:44:

Val Pro Ala Thr Val Tyr Asn Gly Thr Ser Lys Tyr
1               5                   10

Ala Val Gly Gly Ser Gly Arg Arg Gly Asp Met Gly
            15                  20

Ser Leu Ala Ala Arg Val Val Lys Gln Leu Pro Ala
25                  30                  35

Ser Phe Asn Tyr Gly Ala Ile Lys Ala Asp
            40                  45

(2) INFORMATION FOR SEQ ID NO:45:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:45:

Val Leu Ala Thr Val Tyr Asn Gly Val Ser Lys Tyr
1               5                   10

Ala Val Gly Gly Ser Gly Arg Arg Gly Asp Leu Gly
            15                  20

Pro Leu Ala Ala Arg Val Ala Lys Gln Leu Pro Ala
25                  30                  35

Ser Phe Asn Tyr Gly Ala Ile Lys Ala Glu
            40                  45

(2) INFORMATION FOR SEQ ID NO:46:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:46:

Val Leu Ala Thr Val Tyr Asn Gly Thr Asn Lys Tyr
1               5                   10

Thr Val Ser Gly Ser Asn Arg Arg Gly Asp Leu Gly
            15                  20

Ser Leu Ala Ala Arg Val Ala Lys Ala Leu Pro Ala
25                  30                  35

Ser Phe Asn Tyr Gly Ala Ile Lys Ala Asp
            40                  45

(2) INFORMATION FOR SEQ ID NO:47:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:47:

Val Leu Ala Thr Val Tyr Asn Gly Thr Asn Lys Tyr
1               5                   10

Thr Val Ser Gly Ser Asn Arg Arg Gly Asp Leu Gly

```
                15                  20
Pro Leu Ala Ala Arg Val Ala Lys Ala Leu Pro Ala
25                  30                  35

Ser Phe Asn Tyr Gly Ala Ile Lys Ala Asp
                40                  45
```

(2) INFORMATION FOR SEQ ID NO:48:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:48:

```
Val Leu Ala Thr Val Tyr Asn Gly Thr Ser Lys Tyr
1               5                   10

Thr Val Ser Gly Ser Gly Arg Arg Gly Asp Met Gly
                15                  20

Ser Leu Ala Ala Arg Val Val Lys Gln Leu Pro Ala
25                  30                  35

Ser Phe Asn Tyr Gly Ala Ile Lys Ala Asp
                40                  45
```

(2) INFORMATION FOR SEQ ID NO:49:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:49:

```
Val Leu Ala Thr Val Tyr Asn Gly Thr Ser Lys Tyr
1               5                   10

Thr Val Gly Gly Ser Gly Arg Arg Gly Asp Met Gly
                15                  20

Ser Leu Ala Ala Arg Val Ala Lys Gln Leu Pro Ala
25                  30                  35

Ser Phe Asn Phe Gly Ala Val Lys Ala Thr
                40                  45
```

(2) INFORMATION FOR SEQ ID NO:50:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:50:

```
Val Leu Ala Thr Val Asp Asn Gly Thr Ser Lys Tyr
1               5                   10

Thr Val Asp Gly Ser Gly Arg Arg Gly Asp Met Gly
                15                  20

Ser Leu Ala Ala Arg Val Ala Lys Gln Leu Pro Ala
25                  30                  35

Ser Phe Asn Phe Gly Ala Ile Lys Ala Thr
                40                  45
```

(2) INFORMATION FOR SEQ ID NO:51:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:51:

Val Leu Ala Thr Val Tyr Asn Gly Thr Asn Lys Tyr
1               5                   10

Ser Thr Asp Gly Pro Arg Arg Gly Asp Met Gly Ser
            15                  20

Leu Thr Ala Arg Ala Ala Lys Gln Leu Pro Ala Ser
25                      30                  35

Phe Asn Tyr Gly Ala Ile Arg Ala Asp
            40                  45

(2) INFORMATION FOR SEQ ID NO:52:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:52:

Val Leu Ala Thr Val Tyr Asn Gly Thr Asn Lys Tyr
1               5                   10

Ser Thr Gly Gly Ser Arg Arg Gly Asp Thr Gly Ser
            15                  20

Thr Thr Ala Arg Ala Ala Lys Gln Leu Pro Ala Ser
25                      30                  35

Phe Asn Tyr Gly Ala Ile Arg Ala Asp
            40                  45

(2) INFORMATION FOR SEQ ID NO:53:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:53:

Val Leu Ala Thr Val Tyr Asn Gly Thr Asn Lys Tyr
1               5                   10

Ser Thr Asp Gly Pro Arg Arg Asp Met Gly Ser
            15                  20

Pro Ala Ala Arg Ala Ala Lys Gln Leu Pro Ala Ser
25                      30                  35

Phe Asn Tyr Gly Ala Ile Arg Ala Asp
            40                  45

(2) INFORMATION FOR SEQ ID NO:54:

(i) SEQUENCE CHARACTERISTICS:
        (A) LENGTH: 45 amino acids
        (B) TYPE: amino acid (D) TOPOLOGY: linear (ii) MOLECULE TYPE: peptide (xi) SEQUENCE DESCRIPTION: SEQ ID NO:54:

Val Leu Ala Thr Val Tyr Asn Gly Thr Asn Lys Tyr
1               5                   10

Ser Thr Gly Gly Pro Arg Arg Gly Asp Thr Trp Ala
            15                  20

Pro Ala Ala Arg Ala Ala Lys Gln Leu Pro Ala Ser
25                  30                  35

Phe Asn Tyr Gly Ala Ile Arg Ala Asp
            40                  45

(2) INFORMATION FOR SEQ ID NO:55:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:55:

Val Leu Ala Thr Val Tyr Asn Gly Thr Ser Lys Tyr
1               5                   10

Ser Ala Ser Gly Ser Arg Arg Gly Asp Leu Gly Ser
            15                  20

Leu Ala Thr Arg Val Ala Thr Gln Leu Pro Ala Ser
25                  30                  35

Phe Asn Tyr Gly Ala Ile Lys Ala Gln
            40                  45

(2) INFORMATION FOR SEQ ID NO:56:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:56:

Val Leu Ala Thr Val Tyr Asp Gly Thr Asn Lys Tyr
1               5                   10

Ser Ala Ser Asp Ser Arg Ser Gly Asp Leu Gly Ser
            15                  20

Ile Ala Ala Arg Val Ala Thr Gln Leu Pro Ala Ser
25                  30                  35

Phe Asn Tyr Gly Ala Ile Gln Ala Gln
            40                  45

(2) INFORMATION FOR SEQ ID NO:57:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:57:

Val Leu Ala Thr Val Tyr Thr Gly Thr Ser Lys Tyr

```
1               5                   10
Pro Ser Ala Gly Arg Arg Arg Gly Asp Leu Gly Pro
            15                  20

Leu Arg Gln Glu Asp Arg Arg Gln Leu Pro Ala Ser
25                  30                  35

Phe Asn Phe Gly Ala Val Arg Ala Thr
            40                  45
```

(2) INFORMATION FOR SEQ ID NO:58:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:58:

```
Val Leu Ala Asn Val Tyr Asn Arg Thr Gly Arg Ser
1               5                   10

Ser Pro Asp Arg Thr Arg Arg Gly Asp Leu Gly Pro
            15                  20

Pro Leu Ala Arg Tyr Arg Arg Gln Pro Ser Cys Ser
25                  30                  35

Phe Asn Phe Gly Ala Val Arg Ala Thr
            40                  45
```

(2) INFORMATION FOR SEQ ID NO:59:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:59:

```
Val Leu Ala Thr Val Tyr Asn Gly Thr Ser Lys Tyr
1               5                   10

Ser Ala Pro Gly Arg Arg Arg Gly Asp Leu Gly Pro
            15                  20

Leu Leu Gly Glu Asp Arg Arg Gln Leu Pro Ala Ser
25                  30                  35

Phe Asn Phe Gly Ala Val Arg Ala Thr
            40                  45
```

(2) INFORMATION FOR SEQ ID NO:60:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:60:

```
Val Leu Ala Thr Val Tyr Asn Phe Thr Asn Lys Tyr
1               5                   10

Ser Asn Gly Gly Gln Arg Ala Gly Asp Met Gly Ser
            15                  20

Leu Ala Ala Arg Val Ala Lys Gln Leu Pro Ala Ser
25                  30                  35
```

```
Phe Asn Tyr Gly Ala Ile Lys Ala Gln
            40                  45
```

(2) INFORMATION FOR SEQ ID NO:61:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (xi) SEQUENCE DESCRIPTION: SEQ ID NO:61:

```
Leu Ala Thr Val Tyr Asn Gly Thr Ser Lys Tyr Ser
1               5                   10

Ala Ser Gly Leu Gly Pro Gly Asp Leu Gly Ser Pro
        15                  20

Ala Ala Arg Val Ala Thr Gln Leu Pro Ala Ser Phe
25                  30                  35

Asn Tyr Gly Ala Ile Arg Ala Gln
            40
```

(2) INFORMATION FOR SEQ ID NO:62:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:62:

```
Val Leu Ala Thr Val Tyr Asn Gly Thr Asn Lys Tyr
1               5                   10

Ser Thr Asp Gly Pro Arg Arg Gly Asp Met Gly Ser
        15                  20

Leu Thr Ala Arg Ala Ala Lys Gln Leu Pro Xaa Xaa
25                  30                  35

Xaa Asn Tyr Gly Ala Ile Arg Ala Val
            40                  45
```

(2) INFORMATION FOR SEQ ID NO:63:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:63:

```
Val Leu Ala Thr Val Tyr Asn Gly Thr Asn Lys Tyr
1               5                   10

Ser Thr Asp Gly Pro Arg Arg Asp Asp Met Gly Ser
        15                  20

Pro Ala Ala Arg Ala Ala Lys Gln Leu Pro Ala Ser
25                  30                  35

Phe Asn Tyr Gly Ala Ile Arg Ala Val
            40                  45
```

(2) INFORMATION FOR SEQ ID NO:64:

```
       (i) SEQUENCE CHARACTERISTICS:
           (A) LENGTH: 45 amino acids
           (B) TYPE: amino acid
           (D) TOPOLOGY: linear (ii) MOLECULE TYPE: peptide (xi) SEQUENCE DESCRIPTION: SEQ ID NO:64:

Val Leu Ala Thr Val Tyr Asn Gly Thr Asn Lys Tyr
1               5                   10

Ser Thr Asp Gly Pro Arg Arg Gly Asp Met Gly Ser
            15                  20

Leu Thr Ala Arg Ala Ala Lys Gln Leu Pro Ala Ser
25                  30                  35

Phe Asn Tyr Gly Ala Ile Arg Ala Asp
                40                  45

(2) INFORMATION FOR SEQ ID NO:65:

(i) SEQUENCE CHARACTERISTICS:
           (A) LENGTH: 45 amino acids
           (B) TYPE: amino acid
           (D) TOPOLOGY: linear (ii) MOLECULE TYPE: peptide (xi) SEQUENCE DESCRIPTION: SEQ ID NO:65:

Val Leu Ala Thr Val Tyr Asn Gly Thr Asn Lys Tyr
1               5                   10

Ser Thr Gly Gly Ser Arg Arg Gly Asp Thr Gly Ser
            15                  20

Thr Ala Ala Arg Ala Ala Lys Gln Leu Pro Ala Ser
25                  30                  35

Phe Asn Tyr Gly Ala Ile Arg Ala Asp
                40                  45

(2) INFORMATION FOR SEQ ID NO:66:

(i) SEQUENCE CHARACTERISTICS:
           (A) LENGTH: 39 amino acids
           (B) TYPE: amino acid
           (D) TOPOLOGY: linear (ii) MOLECULE TYPE: peptide (xi) SEQUENCE DESCRIPTION: SEQ ID NO:66:

Asn Gly Thr Ser Lys Ser Pro Arg Leu Gly Val Tyr
1               5                   10

Gly Gly Pro Arg Pro Arg Thr Ile Gly Lys Thr Cys
            15                  20

Ala Gln Leu Pro Ala Ser Phe Asn Phe Gly Ala Ile
25                  30                  35

Lys Ala Thr (2) INFORMATION FOR SEQ ID NO:67:

(i) SEQUENCE CHARACTERISTICS:
           (A) LENGTH: 47 amino acids
           (B) TYPE: amino acid
           (D) TOPOLOGY: linear (ii) MOLECULE TYPE: peptide (xi) SEQUENCE DESCRIPTION: SEQ ID NO:67:
```

```
Val Leu Ala Thr Val Tyr Asn Gly Glu Cys Lys Tyr
1               5                   10

Ser Ser Lys Ala Val Pro Asn Val Arg Gly Asp Leu
            15                  20

Asn Val Leu Glu Gln Lys Ala Ala Arg Thr Leu Pro
25                  30                  35

Thr Ser Phe Asn Tyr Gly Ala Ile Lys Ala Thr
                40                  45
```

(2) INFORMATION FOR SEQ ID NO:68:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:68:

```
Val Leu Ala Thr Val Tyr Asn Gly Glu Cys Lys Tyr
1               5                   10

Ser Ser Xaa Ala Val Pro Asn Val Arg Gly Asp Leu
            15                  20

Asn Val Leu Glu Gln Lys Ala Ala Arg Thr Leu Pro
25                  30                  35

Thr Ser Phe Asn Tyr Gly Ala Ile Lys Ala Ser
                40                  45
```

(2) INFORMATION FOR SEQ ID NO:69:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:69:

```
Val Leu Ala Thr Val Tyr Asn Gly Glu Cys Lys Tyr
1               5                   10

Ser Ser Asn Ala Val Pro Asn Val Arg Gly Asp Pro
            15                  20

Asn Val Leu Glu Gln Lys Ala Ala Arg Thr Leu Pro
25                  30                  35

Xaa Xaa Xaa Xaa Xaa Xaa Xaa Xaa Xaa Xaa Thr
                40                  45
```

(2) INFORMATION FOR SEQ ID NO:70:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:70:

```
Val Leu Ala Thr Val Tyr Asn Gly Glu Ser Arg Tyr
1               5                   10

Ser Arg Asn Ala Val Pro Asn Val Arg Gly Asp Leu
            15                  20
```

```
Gln Ala Leu Ala Gln Lys Ala Ala Arg Thr Leu Pro
25                  30                  35

Thr Ser Phe Asn Tyr Gly Ala Ile Arg Ala Thr
            40                  45
```

(2) INFORMATION FOR SEQ ID NO:71:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:71:

```
Val Leu Ala Thr Val Tyr Asn Gly Asn Cys Gln Tyr
1               5                   10

Gly Lys Ser Ser Val Thr Asn Val Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45
```

(2) INFORMATION FOR SEQ ID NO:72:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:72:

```
Val Leu Ala Thr Val Tyr Asn Gly Asn Cys Lys Tyr
1               5                   10

Gly Asp Gly Ala Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45
```

(2) INFORMATION FOR SEQ ID NO:73:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:73:

```
Val Leu Ala Thr Val Tyr Asn Gly Glu Cys Arg Tyr
1               5                   10

Asn Arg Asn Ala Val Pro Asn Leu Arg Gly Asp Leu
            15                  20

Gln Val Leu Ala Gln Lys Val Ala Arg Thr Leu Pro
25                  30                  35

Thr Ser Phe Asn Tyr Gly Ala Ile Lys Ala Thr
            40                  45
```

(2) INFORMATION FOR SEQ ID NO:74:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:74:

Val Leu Ala Thr Val Tyr Asn Gly Glu Cys Arg Tyr
1               5                   10

Gly Glu Ser Ser Val Thr Ala Val Arg Gly Asp Leu
            15                  20

Gln Val Leu Ala Arg Lys Ala Ala Arg Thr Leu Pro
25                  30                  35

Thr Ser Phe Asn Tyr Gly Ala Ile Lys Ala Thr
                40                  45

(2) INFORMATION FOR SEQ ID NO:75:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:75:

Val Leu Ala Thr Val Tyr Asn Gly Asn Cys Arg Tyr
1               5                   10

Gly Glu Ser Ser Val Thr Ala Val Arg Gly Asp Leu
            15                  20

Gln Val Leu Ala Arg Lys Ala Ala Arg Thr Leu Pro
25                  30                  35

Thr Ser Phe Asn Tyr Gly Ala Ile Lys Ala Thr
                40                  45

(2) INFORMATION FOR SEQ ID NO:76:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:76:

Val Leu Ala Ser Cys Tyr Asn Gly Asn Cys Lys Tyr
1               5                   10

Gly Asp Gly Thr Val Thr Asn Ile Arg Gly Asp Gln
            15                  20

Gln Val Leu Ala Gln Lys Ala Ala Arg Ala Leu Pro
25                  30                  35

Thr Ser Phe Asn Tyr Gly Ala Ile Lys Ala Thr
                40                  45

(2) INFORMATION FOR SEQ ID NO:77:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:77:

Val Leu Ala Thr Val Tyr Asn Gly Asn Cys Lys Tyr
1               5                   10

Gly Ser Ser His Val Ala Asn Val Arg Gly Asp Leu
            15                  20

Gln Val Leu Ser Gln Lys Ala Glu Arg Thr Leu Pro
25                  30                  35

Thr Ser Phe Asn Tyr Gly Ala Ile Lys Ala Thr
            40                  45

(2) INFORMATION FOR SEQ ID NO:78:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:78:

Val Leu Ala Thr Val Tyr Asn Gly Asn Cys Arg Tyr
1               5                   10

Gly Asn Val Ala Val Thr Asn Val Arg Gly Asp Leu
            15                  20

Gln Val Leu Ala Gln Lys Ala Ala Arg Thr Leu Pro
25                  30                  35

Thr Ser Phe Asn Tyr Gly Ala Ile Lys Xaa Thr
            40                  45

(2) INFORMATION FOR SEQ ID NO:79:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:79:

Val Leu Ala Thr Val Tyr Asn Gly Glu Cys Thr Tyr
1               5                   10

Ser Ser Asn Ala Val Pro Asn Val Arg Gly Asp Pro
            15                  20

Asn Leu Leu Glu Gln Lys Ala Ala Arg Met Leu Pro
25                  30                  35

Ala Tyr Phe Asn Tyr Gly Ala Ile Lys Ala Thr
            40                  45

(2) INFORMATION FOR SEQ ID NO:80:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:80:

Val Leu Ala Thr Val Tyr Asn Gly Glu Cys Arg Tyr
1               5                   10

Ser Arg Asn Ala Val Pro Asn Leu Arg Gly Asp Leu
            15                  20

Gln Val Leu Ala Gln Lys Val Ala Arg Thr Leu Pro
25                  30                  35

Thr Ser Phe Asn Tyr Gly Ala Ile Lys Ala Thr
            40                  45

(2) INFORMATION FOR SEQ ID NO:81:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:81:

Val Leu Ala Thr Val Tyr Asn Gly Asn Cys Lys Tyr
1               5                   10

Gly Glu Asn Ser Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45

(2) INFORMATION FOR SEQ ID NO:82:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:82:

Val Leu Ala Thr Val Tyr Asn Gly Asn Cys Lys Tyr
1               5                   10

Gly Thr Asn Ala Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45

(2) INFORMATION FOR SEQ ID NO:83:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:83:

Val Leu Ala Thr Val Tyr Asn Gly Asn Cys Lys Tyr
1               5                   10

Gly Glu Ser Ser Val Thr Asn Val Arg Gly Asp Leu
            15                  20

Gln Val Leu Ala Gln Lys Ala Ala Arg Thr Leu Pro
25                  30                  35

Thr Ser Phe Asn Tyr Gly Ala Ile Lys Ala Thr 40                  45

(2) INFORMATION FOR SEQ ID NO:84:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:84:

Val Leu Ala Thr Val Tyr Gln Arg Asn Cys Lys Tyr
1               5                   10

Gly Asp Gly Ala Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45

(2) INFORMATION FOR SEQ ID NO:85:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:85:

Val Leu Ala Ser Val Tyr Tyr Gly Tyr Cys Lys Tyr
1               5                   10

Gly Asp Gly Gly Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45

(2) INFORMATION FOR SEQ ID NO:86:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:86:

Val Leu Ala Thr Val Tyr Asn Arg Asn Cys Lys Tyr
1               5                   10

Gly Glu Trp Ser Val Thr Asn Ile Arg Gly Asp Leu
            15                  20

Gln Val Leu Ala Gln Lys Ala Ala Arg Ala Leu Pro
25                  30                  35

Thr Ser Phe Asn Tyr Gly Ala Ile Lys Ala Thr
            40                  45

(2) INFORMATION FOR SEQ ID NO:87:

(i) SEQUENCE CHARACTERISTICS:
        (A) LENGTH: 45 amino acids (B) TYPE: amino acid
            (D) TOPOLOGY: linear (ii) MOLECULE TYPE: peptide (xi) SEQUENCE DESCRIPTION: SEQ ID NO:87:

Val Leu Ala Thr Val Tyr Asn Gly Lys Thr Thr Tyr
1               5                   10

Gly Thr Gln Pro Thr Arg Arg Gly Asp Leu Ala Val
            15                  20

Leu Ala Gln Arg Val Ser Asn Arg Leu Pro Thr Ser
25                  30                  35

Phe Asn Tyr Gly Ala Val Lys Ala Asp
            40                  45

(2) INFORMATION FOR SEQ ID NO:88:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:88:

Val Leu Ala Thr Val Tyr Asn Gly Lys Pro Thr Tyr
1               5                   10

Gly Lys Gln Pro Ser Arg Arg Gly Asp Met Ala Ala
            15                  20

Leu Ala Gln Arg Leu Ser Arg Gln Leu Pro Thr Ser
25                  30                  35

Phe Asn Tyr Gly Ala Val Lys Ala Glu
            40                  45

(2) INFORMATION FOR SEQ ID NO:89:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:89:

Val Leu Ala Thr Val Tyr Asn Gly Lys Thr Thr Tyr
1               5                   10

Gly Glu Gln Pro Ser Arg Arg Gly Asp Met Ala Ala
            15                  20

Leu Ala Gln Arg Leu Ser Arg Gln Leu Pro Thr Ser
25                  30                  35

Phe Asn Tyr Gly Ala Val Lys Ala Glu
            40                  45

(2) INFORMATION FOR SEQ ID NO:90:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:90:

```
Val Leu Ala Thr Val Tyr Asn Gly Lys Thr Thr Tyr
1               5                   10

Gly Thr Gln Pro Thr Arg Arg Gly Asp Leu Ala Val
            15                  20

Leu Ala Gln Arg Val Ser Asn Arg Leu Pro Thr Ser
25                  30                  35

Phe Asn Tyr Gly Ala Val Lys Ala Asp
            40              45

(2) INFORMATION FOR SEQ ID NO:91:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:91:

Val Leu Ala Thr Val Tyr Asn Gly Lys Arg Pro Tyr
1               5                   10

Gly Glu Thr Thr Ser Arg Arg Gly Asp Met Ala Ala
            15                  20

Leu Ala Gln Arg Leu Ser Ala Arg Leu Pro Thr Ser
25                  30                  35

Phe Asn Tyr Gly Ala Val Lys Ala Asp
            40              45
```